US012799336B2

(12) United States Patent
Neya et al.

(10) Patent No.: US 12,799,336 B2
(45) **Date of Patent: *Nov. 17, 2026**

(54) SURFACE-TREATED METAL OXIDE PARTICLES, DISPERSION LIQUID, COSMETIC AND METHOD FOR PRODUCING SURFACE-TREATED METAL OXIDE PARTICLES

(71) Applicant: SUMITOMO OSAKA CEMENT CO., LTD., Tokyo (JP)

(72) Inventors: Tadashi Neya, Tokyo (JP); Hirokazu Matsushita, Tokyo (JP)

(73) Assignee: SUMITOMO OSAKA CEMENT CO., LTD., Tokyo (JP)

( * ) Notice: Subject to any disclaimer, the term of this patent is extended or adjusted under 35 U.S.C. 154(b) by 814 days.

This patent is subject to a terminal disclaimer.

(21) Appl. No.: 17/913,422

(22) PCT Filed: Mar. 25, 2021

(86) PCT No.: PCT/JP2021/012548

§ 371 (c)(1),
(2) Date: Sep. 21, 2022

(87) PCT Pub. No.: WO2021/200541

PCT Pub. Date: Oct. 7, 2021

(65) Prior Publication Data

US 2023/0136530 A1 May 4, 2023

(30) Foreign Application Priority Data

Mar. 31, 2020 (JP) ................................ 2020-061760
Mar. 31, 2020 (JP) ................................ 2020-062422

(51) Int. Cl.

*C09C 3/12* (2006.01)
*A61K 8/27* (2006.01)
*A61Q 17/04* (2006.01)

(52) U.S. Cl.

CPC .................. *C09C 3/12* (2013.01); *A61K 8/27* (2013.01); *A61Q 17/04* (2013.01)

(58) Field of Classification Search

CPC .............. C09C 3/12; A61K 8/27; A61Q 17/04
See application file for complete search history.

(56) References Cited

U.S. PATENT DOCUMENTS 11,325,840 B1 * 5/2022 Neya ...................... A61Q 19/00
2010/0188766 A1 7/2010 Haimoto et al.
(Continued)

FOREIGN PATENT DOCUMENTS

CN 102492173 A 6/2012
EP 2027847 A1 * 2/2009 ............... A61K 8/49
(Continued)

OTHER PUBLICATIONS

Machine translation of JP 2000319128 from PE2E via FIT, 2000 (Year: 2000).*

(Continued)

*Primary Examiner* — Isis A Ghali
*Assistant Examiner* — Ayaan A Alam
(74) *Attorney, Agent, or Firm* — Merchant & Gould P.C.

(57) ABSTRACT

These surface-treated metal oxide particles are metal oxide particles surface-treated with a silane coupling agent having an alkoxy group, in which the metal oxide particles have an ultraviolet shielding property, a weight loss of the surface-treated metal oxide particles on drying at 105° C. for 3 hours is 0.5% by mass or less, a peak derived from the alkoxy group is not detected in a reflection spectrum of the surface-treated metal oxide particles in 900 $cm^{-1}$ to 1300 $cm^{-1}$, which is measured by a Fourier transform infrared spectrophotometer, and a value (D98/BET converted diameter)

(Continued)

obtained by dividing a dry particle size D98 (μm) thereof by a BET-converted particle diameter (nm) thereof is 0.01 or more and 5.0 or less.

18 Claims, 3 Drawing Sheets

(56) References Cited

U.S. PATENT DOCUMENTS

| | | | |
|---|---|---|---|
| 2012/0027709 | A1 | 2/2012 | Sato et al. |
| 2014/0044971 | A1 | 2/2014 | Sueda et al. |
| 2025/0197239 | A1 | 6/2025 | Neya et al. |

FOREIGN PATENT DOCUMENTS

| | | | |
|---|---|---|---|
| JP | 11-181329 | A | 7/1999 |
| JP | 2000-319128 | A | 11/2000 |
| JP | 2001-181136 | A | 7/2001 |
| JP | 2002-212462 | A | 7/2002 |
| JP | 2002-362925 | A | 12/2002 |
| JP | 2007-045859 | A | 2/2007 |
| JP | 2007-051188 | A | 3/2007 |
| JP | 2008-303231 | A | 12/2008 |
| JP | 2009-208988 | A | 9/2009 |
| JP | 2010-241732 | A | 10/2010 |
| JP | 2019-099510 | A | 6/2019 |
| WO | 2012/147888 | A1 | 11/2012 |
| WO | 2017/130632 | A1 | 8/2017 |

OTHER PUBLICATIONS

Sakamoto, Influence of particle size of titanium dioxide on UV-ray shielding property, 1996, KONA, 14, 183-189 (Year: 1996).*

International Search Report for PCT/JP2021/012548 (May 25, 2021).

Supplementary European Search Report for EP Application No. 21778794.4 (Oct. 14, 2024).

International search report of PCT/JP2022/018859, mailed on Jul. 12, 2022, with English translation, 4 pages.

* cited by examiner

SURFACE-TREATED METAL OXIDE PARTICLES, DISPERSION LIQUID, COSMETIC AND METHOD FOR PRODUCING SURFACE-TREATED METAL OXIDE PARTICLES

TECHNICAL FIELD

The present invention relates to surface-treated metal oxide particles, a dispersion liquid, a cosmetic and a method for producing surface-treated metal oxide particles.

This application is a National Stage Application of PCT/JP2021/012548, filed Mar. 25, 2021, which claims benefit of priority to Japanese Patent Application No. 2020-061760 and Japanese Patent Application No. 2020-062422, filed in Japan on Mar. 31, 2020, the contents of which are incorporated herein by reference. To the extent appropriate, a claim of priority is made to each of the above disclosed applications.

BACKGROUND ART

Metal oxide particles having an ultraviolet shielding property of zinc oxide, titanium oxide or the like are in use in cosmetics such as sunscreens and foundations.

In a case where these metal oxide particles are applied to cosmetics, a surface treatment is performed on the metal oxide particles in order to adapt the surface state of the metal oxide particles to the properties of cosmetic products or suppress the catalytic activity of the metal oxide particles. As a surface treatment agent for such metal oxide particles, for example, a metal soap such as magnesium stearate, a silicone oil such as dimethicone or hydrogen dimethicone, a silane coupling agent having an alkoxy group such as octyltriethoxysilane, or the like can be used (for example, refer to Patent Literature 1 and 2).

Metal oxide particles surface-treated with, among them, the silane coupling agent are highly stable since the silane coupling agent, which is a surface treatment agent, chemically bonds to the surfaces of the metal oxide particles.

Furthermore, the metal oxide particles as described above can be easily changed in the properties of the particle surfaces by using a surface treatment agent having different substituents. In the following description, metal oxide particles surface-treated with a silane coupling agent will be referred to as surface-treated metal oxide particles.

Such surface-treated metal oxide particles are blended with cosmetics as they are or blended with cosmetics in a state of a dispersion liquid in which the metal oxide particles are dispersed in a dispersion medium.

CITATION LIST

Patent Literature

[Patent Literature No. 1] Japanese Laid-open Patent Publication No. 2002-362925
[Patent Literature No. 2] Japanese Laid-open Patent Publication No. 2001-181136.

SUMMARY OF INVENTION

Technical Problem

However, there has been a problem in that the surface-treated metal oxide particles have a poor ultraviolet shielding property in some cases when blended with cosmetics and the quality regarding the ultraviolet shielding property is difficult to stabilize. In particular, in a case where metal oxide particles having a large BET specific surface area are used, in a case where the amount of a surface treatment agent is increased, or in a case where surface-treated metal oxide particles are stored for a long period of time, there has been a problem in that the ultraviolet shielding property of the surface-treated metal oxide particles significantly deteriorates.

In addition, there has been a problem in that, when a cosmetic containing the surface-treated metal oxide particles is applied to the skin, there are cases where a rough feeling is felt and the quality regarding touch-and-feel is difficult to stabilize.

Therefore, there has been a demand for surface-treated metal oxide particles by which the deterioration of the ultraviolet shielding property is prevented while the rough feeling is prevented.

The present invention has been made in view of the above-described circumstances, and an object of the present invention is to provide surface-treated metal oxide particles that stably exhibit a high ultraviolet shielding property and suppress a rough feeling. In addition, another object of the present invention is to provide a dispersion liquid and a cosmetic which contain such surface-treated metal oxide particles. In addition, still another object of the present invention is to provide a method for producing such surface-treated metal oxide particles.

Solution to Problem

In order to achieve the above-described objects, a first aspect of the present invention provides surface-treated metal oxide particles surface-treated with a silane coupling agent having an alkoxy group,

- in which the metal oxide particles have an ultraviolet shielding property,
- a weight loss of the surface-treated metal oxide particles on drying at 105° C. for 3 hours is 0.5% by mass or less,
- a peak derived from the alkoxy group is not detected in a reflection spectrum of the surface-treated metal oxide particles in 900 $cm^{-1}$ to 1300 $cm^{-1}$, which is measured by a Fourier transform infrared spectrophotometer, and
- a value (D98/BET converted diameter) obtained by dividing a dry particle size D98 (μm) thereof by a BET-converted particle diameter (nm) thereof is 0.01 or more and 5.0 or less.

A second aspect of the present invention provides a dispersion liquid containing the surface-treated metal oxide particles and a dispersion medium.

A third aspect of the present invention provides a cosmetic containing at least one kind selected from the group consisting of the surface-treated metal oxide particles and the dispersion liquid.

A fourth aspect of the present invention is a method for producing metal oxide particles surface-treated with a silane coupling agent having an alkoxy group,

- in which the metal oxide particles have an ultraviolet shielding property,
- the method includes a step of forming surface-treated metal oxide particles, and
- a step of determining whether or not a peak derived from the alkoxy group is detected in a reflection spectrum of the surface-treated metal oxide particles in 900 $cm^{-1}$ to 1300 $cm^{-1}$, which is measured with a Fourier transform infrared spectrophotometer.

Advantageous Effects of Invention

According to the present invention, it is possible to provide surface-treated metal oxide particles that stably exhibit a high ultraviolet shielding property and suppress a rough feeling. In addition, according to the present invention, it is possible to provide a dispersion liquid and a cosmetic which contain such surface-treated metal oxide particles. In addition, according to the present invention, it is possible to provide a method for producing such surface-treated metal oxide particles.

DESCRIPTION OF EMBODIMENTS

Figure 1:
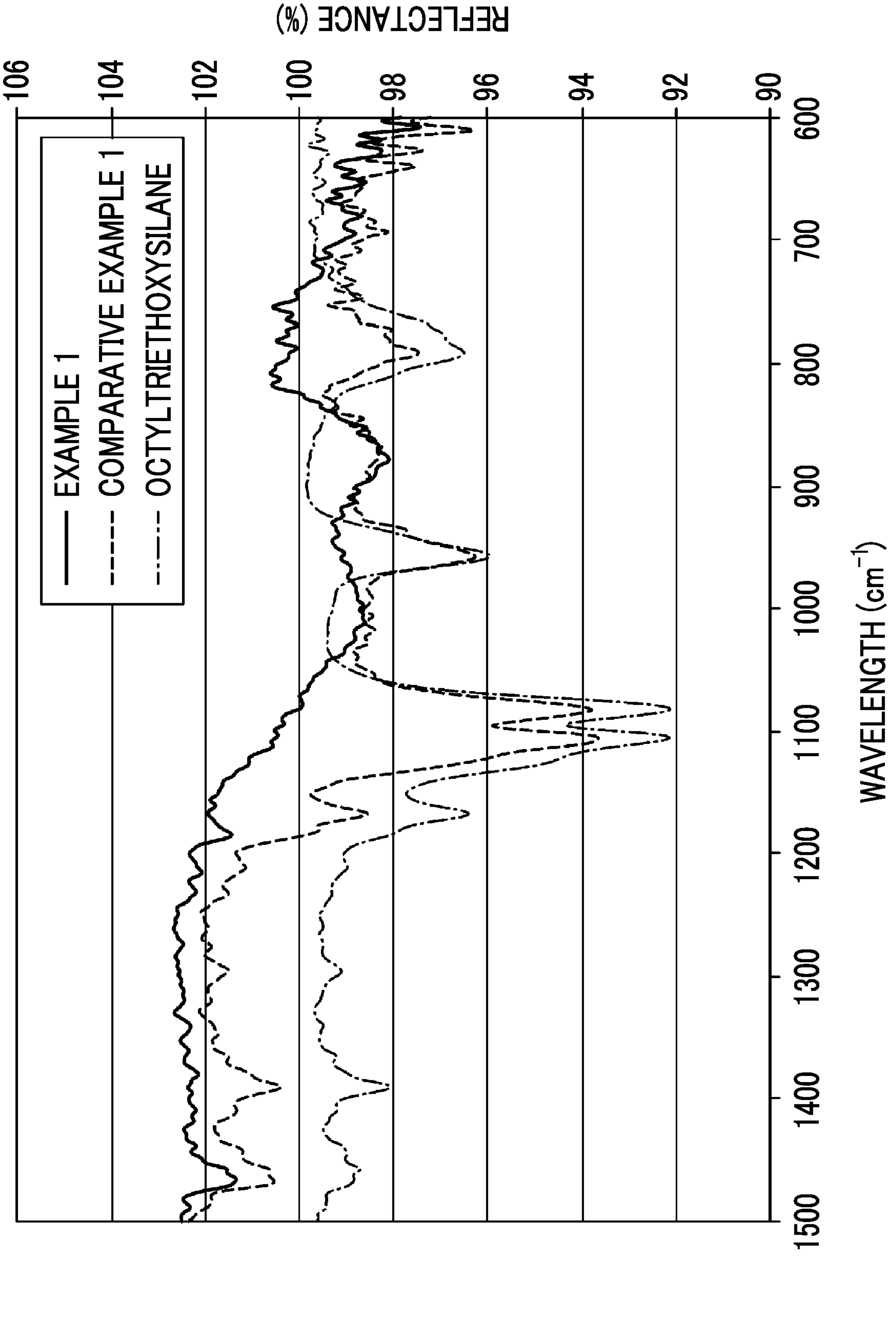
FIG. 1 is a view showing measurement results with FT-IR of surface-treated zinc oxide particles of Example 1, surface-treated zinc oxide particles of Comparative Example 1, and octyltriethoxysilane.

Examples of preferable embodiments of surface-treated metal oxide particles, a dispersion liquid, a cosmetic, and a method for producing surface-treated metal oxide particles of the present invention will be described.

The present embodiment is simply a specific description for better understanding of the gist of the invention and does not limit the present invention unless particularly otherwise described. For example, unless particularly otherwise described, conditions such as materials, amounts, kinds, numbers, sizes, ratios, and temperatures and the like may be changed, added, and omitted as necessary. Preferable examples may be exchanged or shared between embodiments to be described below.

In the following description, there are cases where surface-treated metal oxide particles are abbreviated as "surface-treated particles".

[Surface-Treated Metal Oxide Particles]

Surface-treated metal oxide particles of the present embodiment are metal oxide particles that are surface-treated with a silane coupling agent having an alkoxy group and have an ultraviolet shielding property. The metal oxide particles have an ultraviolet shielding property, and the weight loss of the surface-treated metal oxide particles on drying at 105° C. for 3 hours is 0.5% by mass or less. Furthermore, in a reflection spectrum of these surface-treated metal oxide particles in 900 $cm^{-1}$ to 1300 $cm^{-1}$, which is measured with a Fourier transform infrared spectrophotometer (FT-IR), a peak derived from the alkoxy group is not detected.

Furthermore, a value (D98/BET converted diameter) obtained by dividing the dry particle size D98 (μm) of these surface-treated metal oxide particles by the BET-converted particle diameter (nm) is 0.01 or more and 5.0 or less.

(Reflection Spectrum of Surface-Treated Metal Oxide Particles)

The peak derived from the alkoxy group means a peak that is ordinarily detected within a range of 900 $cm^{-1}$ to 1300 $cm^{-1}$ in the case of measuring the silane coupling agent having the alkoxy group by an attenuated total reflectance method (ATR method) with FT-IR.

Regarding the detection of the presence or absence of a peak, in detail, a peak of the alkoxy group needs to be identified using "Identification method by spectrum of organic compound, 6th edition" in consideration of the structure of the silane coupling agent having the alkoxy group.

Peaks that are the peak derived from the alkoxy group and are preferably not detected are 1170 $cm^{-1}$, 1100 $cm^{-1}$, 1080 $cm^{-1}$, and 950 $cm^{-1}$. It is preferable that at least one of these peaks is not detected, and it is more preferable that all peaks are not detected.

These peaks are peaks that are detected within a range of 900 $cm^{-1}$ to 1300 $cm^{-1}$ when octyltriethoxysilane, which is an example of the silane coupling agent having an alkoxy group, is measured with FT-IR.

In the present specification, "peak is not detected" means that the reflectance of the peak top is 1% or less (−1% or more and 0% or less) in absolute value when the reflectance of the baseline is defined as 0%.

In addition, in the present specification, for example, the fact that a peak is not detected at 950 $cm^{-1}$ means that a peak including 950 $cm^{-1}$ in the range is not detected. That is, it does not mean that a peak having the peak top at 950 $cm^{-1}$ is not detected. What has been described above is understood in the same manner for 1170 $cm^{-1}$, 1100 $cm^{-1}$, and 1080 $cm^{-1}$.

As described above, there will be cases where "Fourier transform infrared spectrophotometer" is abbreviated as "FT-IR".

The technical meaning of the peak derived from the alkoxy group being not detected in the spectrum measured with the Fourier transform infrared spectrophotometer will be described below.

The fact that, in a case where metal oxide particles surface-treated with a silane coupling agent having an alkoxy group are measured with FT-IR, a peak derived from this alkoxy group is not observed means that the alkoxy group of the silane coupling agent does not remain in the surface-treated metal oxide particles.

In the present embodiment, a silane coupling agent containing an appropriate amount of an alkoxy group is used, and a hydrolysis reaction thereof is caused, thereby surface-treating metal oxide particles. Therefore, from the fact that the alkoxy groups do not remain in the obtained surface-treated metal oxide particles, it is presumed that almost all of the alkoxy groups in the silane coupling agent used undergo a hydrolysis reaction to react with OH groups present on the surfaces of the metal oxide particles. In addition, as a result, it is presumed that the number of OH groups remaining in the surface-treated metal oxide particles is small or OH groups do not remain.

In addition, according to the surface-treated metal oxide particles of the present embodiment, since there are no or an extremely small number of alkoxy groups, it is presumed that it is possible to prevent the following event in a case where the surface-treated metal oxide particles are stored; the alkoxy groups remaining in the particles are hydrolyzed by moisture in the atmosphere, and, as a result, the number of OH groups in the surface-treated metal oxide particles increases.

(Weight Loss on Drying of Surface-Treated Metal Oxide Particles)

The weight loss of the surface-treated metal oxide particles of the present embodiment on drying at 105° C. for 3 hours is 0.5% by mass or less and preferably 0.4% by mass or less. The lower limit value of the weight loss on drying can be arbitrarily selected, and may be, for example, 0.00% by mass, 0.01% by mass, 0.03% by mass, or 0.05% by mass.

When the weight loss on drying at 105° C. for 3 hours is 0.5% by mass or less, the dispersion stability in compositions containing a water-based volatile component and an oil-based component of the surface-treated metal oxide particles is maintained. In addition, in the case of being applied to an object (the skin in the case of cosmetics), a composition containing the surface-treated metal oxide particles is capable of exhibiting a high ultraviolet shielding property.

The weight loss of the surface-treated metal oxide particles on drying at 105° C. for 3 hours can be obtained by the following method.

First, 2 g of the surface-treated metal oxide particles are prepared. These surface-treated metal oxide particles are preferably particles that are stored under dry conditions. The dry conditions may mean that, for example, the surface-treated metal oxide particles are stored in a desiccator with silica gel therein or an aluminum bag with silica gel therein. These particles are heated in a dryer set at 105° C. for 3 hours, the mass after the heating is measured, and the mass reduction rate can be defined as the weight loss on drying (% by mass).

That is, the weight loss on drying can be obtained from the following formula (1).

Weight loss on drying (% by mass) of surface-treated metal oxide particles=(mass of surface-treated metal oxide particles before heating−mass of surface-treated metal oxide particles after heating)/mass of surface-treated metal oxide particles before heating×100 (1)

(Ultraviolet Shielding Property (UV Transmittance) of Surface-Treated Metal Oxide Particles)

The present inventors and the like found that, when surface-treated metal oxide particles from which a peak derived from the alkoxy group is not detected in a reflection spectrum in 900 $cm^{-1}$ to 1300 $cm^{-1}$ measured with FT-IR and of which the weight loss on drying at 105° C. for 3 hours is 0.5% by mass or less is blended with a cosmetic, the ultraviolet shielding property of the surface-treated metal oxide particles is extremely high.

The reason therefor is presumed as described below.

The silane coupling agent preferably contains one or more alkoxy groups. The metal oxide particle contains an oxygen atom and has a OH group attributed to the oxygen atom on the surface.

Generally, cosmetics are used in an oil in water form (W/O form) or a water in oil form (O/W form). In surface-treated metal oxide particles from which a peak derived from the alkoxy group is detected and of which the weight loss on drying exceeds 0.5% by mass, it is presumed that a large number of OH groups are contained in the surface-treated metal oxide particles. It is presumed that, in a process of applying and drying a cosmetic containing such particles blended with an oil phase to and on the skin, the surface-treated metal oxide particles are likely to agglomerate together in the oil phase due to the influence of the OH groups and it becomes difficult to impart a desired ultraviolet shielding property to the skin.

That is, in a case where the weight loss on drying is large, it is considered that the alkoxy groups of the added silane coupling agent and the OH groups do not sufficiently react with each other and a large number of the OH groups remain on the surfaces of the metal oxide particles surface-treated with the silane coupling agent. In addition, in a case where a peak derived from the alkoxy group is detected in addition to the above-described state, it is presumed that alkoxy groups that have not reacted with the OH groups in the metal oxide particles are present.

However, in the case of the surface-treated metal oxide particle of the present embodiment from which the peak derived from the alkoxy group is not detected and of which the weight loss on drying is 0.5% by mass or less, the number of OH groups in the surface-treated metal oxide particles is small and does not positively increase. Therefore, it is presumed that the surface-treated metal oxide particles of the present embodiment are less likely to agglomerate together and are capable of stably exhibit a high ultraviolet shielding property.

That is, in a case where the weight loss on drying is small, it is considered that the number of OH groups on the surfaces of the surface-treated metal oxide particles is small, that is, the alkoxy groups of the added silane coupling agent and the OH groups sufficiently react with each other. In addition, in a case where a peak derived from the alkoxy group is not detected in addition to the above-described state, it is presumed that alkoxy groups that are contained in the silane coupling agent have efficiently reacted with the OH groups.

In a case where the amount of the silane coupling agent is too small with respect to the surface-treated metal oxide particles, it is presumed that the amount of the OH groups on the surfaces of the surface-treated metal oxide particles increases and a peak of the alkoxy group is not observed. In a case where the amount of the silane coupling agent is too large, it is presumed that the amount of the OH group decreases, but a peak of the alkoxy group is observed. However, the residual silane coupling agent can be removed or cleaned by an arbitrarily selected method in a case where the fact that the silane coupling agent remains is found.

In addition, in a case where the amount of the silane coupling agent is appropriate, but the treatment conditions are not appropriate, it is presumed that the amount of the OH group increases and a peak of the alkoxy group is also observed.

In a case where the amount of the OH group decreases, but the alkoxy group is detected, this means that excess alkoxy groups remain, and, in a case where the surface-treated metal oxide particles have been stored, the residual alkoxy groups are hydrolyzed by moisture in the atmosphere, which acts as a cause for increasing the number of OH groups in the surface-treated metal oxide particles, which is not preferable.

In the present invention, having an ultraviolet shielding property means having an effect of shielding at least any range in the ultraviolet (10 nm to 400 nm) region. Examples of a method for evaluating the presence or absence of the ultraviolet shielding property include a method in which a transmission spectrum is measured in a wavelength region of ultraviolet rays of a coated film containing 10% by mass of the metal oxide particles, for example, a wavelength region of 10 nm to 450 nm, more specifically, a wavelength region of 250 nm to 450 nm. In the case of having an ultraviolet shielding property, there is a region where the transmittance in a wavelength region of 250 nm to 400 nm becomes lower than the transmittance at 450 nm.

Whether or not the surface-treated metal oxide particles have an ultraviolet shielding property may be determined by, for example, the following steps (1) to (3). However, the method is not limited only to this example. (1) A dispersion liquid containing 10 parts by mass of the surface-treated metal oxide particles is applied such that the thickness after drying becomes 12 μm and is applied onto, for example, a quartz glass plate to obtain a film. As a specific example, 10 parts by mass of the surface-treated metal oxide particles and 90 parts by weight of a liquid, for example, 2 parts by mass of PEG-9 polydimethylsiloxyethyl dimethicone and 88 parts by mass of decamethylcyclopentasiloxane are mixed together, and the mixture is applied such that the thickness after drying becomes 12 μm to obtain a film. (2) The transmission spectrum of the film is measured to obtain the average transmittance A of the film in a range of 250 nm to 400 nm and the transmittance B of the film at 450 nm. (3) In a case where the transmittance A is lower than the transmittance B, the surface-treated metal oxide particles are determined to have an ultraviolet shielding property.

The surface-treated metal oxide particles of the above embodiment are usually composed of secondary particles, but may contain primary particles.

(D98 (μm)/BET-Converted Particle Diameter (Nm) of Surface-Treated Metal Oxide Particles)

In the surface-treated metal oxide particles of the present embodiment, the value (D98 (μm)/BET-converted particle diameter (nm)) obtained by dividing the dry particle size D98 (μm) of the surface-treated metal oxide particles by the BET-converted particle diameter (nm) of the surface-treated metal oxide particles is 0.01 or more and 5 or less. Hereinafter, there will be cases where "dry particle size D98 (μm)" is abbreviated as "D98" and "BET-converted particle diameter (nm)" is abbreviated as "converted diameter".

In the present specification, "D98" means a value of the powder particle size at a cumulative volume percentage of 98% when the volume particle size distribution is measured in a dry manner using a laser diffraction-type particle size distribution-measuring instrument, for example, a laser diffraction-type particle size distribution-measuring instrument (Model No.: Mastersizer 3000, manufactured by Malvern Panalytical Ltd.).

In the present specification, "BET-converted particle diameter (nm)" means a particle diameter of the BET specific surface area ($m^2/g$) of the surface-treated metal oxide particles converted using the following general formula (2).

$$BET\text{-converted particle diameter (nm)}=6000/(BET\ \text{specific surface area}(m^2/g)\times\rho(g/cm^3)) \quad (2)$$

In the formula (2), ρ is the density of the metal oxide particle.

For example, ρ of zinc oxide is 5.61 $g/cm^3$ and ρ of titanium oxide is 4.23 $g/cm^3$.

In addition, the BET specific surface area means a value measured by the BET method using a specific surface area-measuring instrument, for example, a full automatic specific surface area-measuring instrument (trade name: Macsorb HM Model-1201 manufactured by Mountech Co., Ltd.).

In the surface-treated metal oxide particles of the present embodiment, the value of the D98/BET-converted particle diameter is 0.01 or more and 5.0 or less, preferably 0.01 or more and 4.5 or less, and more preferably 0.01 or more and 3.0 or less. The values may be 0.05 or more and 2.5 or less, 0.1 or more and 2.3 or less, 0.2 or more and 2.0 or less, or 0.5 or more and 1.5 or less as necessary. When the D98/converted diameter is within the above-described range, the rough feeling of the surface-treated metal oxide particles can be suppressed.

The reason that the rough feeling can be suppressed when the D98/converted diameter is within the above-described range is presumed that the difference in size between coarse particles and the average particle is that large and an appropriate particle size distribution can be obtained.

(BET Specific Surface Area of Surface-Treated Metal Oxide Particles)

The BET specific surface area of the surface-treated metal oxide particles can be arbitrarily selected, but is preferably 1.5 $m^2/g$ or more, more preferably 2.5 $m^2/g$ or more, and still more preferable 4 $m^2/g$ or more. The BET specific surface area of the surface-treated metal oxide particles is preferably 65 $m^2/g$ or less and more preferably 60 $m^2/g$ or less.

If necessary, the BET specific surface area of the surface-treated metal oxide particles may be 55 $m^2/g$ or less, 50 $m^2/g$ or less, 45 $m^2/g$ or less, 30 $m^2/g$ or less, or 10 $m^2/g$ or less. The upper limit value and lower limit value of the BET specific surface area of the surface-treated metal oxide particles can be arbitrarily combined.

When the BET specific surface area of the surface-treated metal oxide particles is 1.5 $m^2/g$ or more and 65 $m^2/g$ or less, the surface-treated metal oxide particles are excellent in terms of the transparency and the ultraviolet shielding property in the case of being blended with cosmetics. When the BET specific surface area of the surface-treated metal oxide particles is 1.5 $m^2/g$ or more and 65 $m^2/g$ or less, the BET-converted particle diameter (nm) obtained from the formula (2) is about 16.5 nm or more and 713 nm or less.

In a case where there is a desire to enhance the transparency in the case of blending the surface-treated metal oxide particles with cosmetics, the BET specific surface area of the surface-treated metal oxide particles is preferably 8 $m^2/g$ or more, more preferably 15 $m^2/g$ or more, and still more preferable 20 $m^2/g$ or more. On the other hand, in a case where there is a desire to enhance the UVA shielding property in the case of blending the surface-treated metal oxide particles with cosmetics, the BET specific surface area of the surface-treated metal oxide particles is preferably less than 8 $m^2/g$, more preferably 7.5 $m^2/g$ or less, and still more preferably 7.0 $m^2/g$ or less.

(Average Primary Particle Diameter of Surface-Treated Metal Oxide Particles)

The average primary particle diameter of the surface-treated metal oxide particles of the present embodiment can be arbitrarily selected, but is preferably 15 nm or more, and more preferably 20 nm or more. In addition, the average primary particle diameter of the surface-treated metal oxide particles is preferably 715 nm or less and more preferably 650 nm or less. The average primary particle diameter may be 550 nm or less, 350 nm or less, 250 nm or less, or 180 nm or less as necessary.

When the average primary particle diameter of the surface-treated metal oxide particles is 15 nm or more and 715 nm or less, the surface-treated metal oxide particles are excellent in terms of the transparency and the ultraviolet shielding property in the case of being blended with cosmetics. In a case where there is a desire to enhance the transparency in the case of blending the surface-treated metal oxide particles with cosmetics, the average primary particle diameter of the surface-treated metal oxide particles is preferably 135 nm or less, more preferably 100 nm or less, and still more preferably 50 nm or less. On the other hand, in a case where there is a desire to enhance the UVA shielding property in the case of blending the surface-treated metal oxide particles with cosmetics, the primary particle diameter of the surface-treated metal oxide particles is preferably more than 135 nm, more preferably 140 nm or more, and still more preferably 150 nm or more.

The average primary particle diameter of the surface-treated metal oxide particles approximately coincides with the BET-converted particle diameter (nm) of the surface-treated metal oxide particles, but may be obtained by the following method. First, the surface-treated metal oxide particles are observed using a transmission electron microscope (TEM) or the like. In addition, a predetermined number of, for example, 200 or 100, surface-treated metal oxide particles are selected. In addition, the longest linear portion (maximum major axis) of each of these surface-treated metal oxide particles is measured, and these measurement values are arithmetically averaged to obtain the average primary particle diameter.

In a case where the surface-treated metal oxide particles agglomerate together, the measurement subject is not the agglomerated particle diameter of this agglomerate. A predetermined number of surface-treated metal oxide particles (primary particles) that configure this agglomerate are measured to obtain the average primary particle diameter.

(Si CP/MAS-NMR Spectrum)

For the surface-treated metal oxide particles of the present embodiment, in a spectrum measured by the solid-state $^{29}$Si CP/MAS-nuclear magnetic resonance (NMR) spectroscopy, when the integral value of the spectrum within a measurement range of −30 ppm to −60 ppm is defined as 100, a value obtained by dividing the integral proportion of the spectrum within a measurement range of −50 ppm to −60 ppm by the integral proportion of the spectrum within a measurement range of −40 ppm to −50 ppm is preferably 0.5 or more and 5.0 or less.

The Si CP/MAS-NMR spectrum of the surface-treated metal oxide particles can be obtained by the CP/MAS method. The CP/MAS method is a method in which the magnetization of a $^{29}$Si nucleus having a long relaxation time is shifted to $^{1}$H having a short relaxation time and observed. The CP/MAS method has an advantage of improving the integration efficiency and the sensitivity by the shortening of the pulse delay. Therefore, even in a case where the relaxation time is long and the abundance is small as in the $^{29}$Si nucleus attributed to the silane coupling agent in the surface-treated metal oxide particles, a Si CP/MAS-NMR spectrum can be obtained. The CP/MAS method has a disadvantage in that it becomes difficult to observe a signal of Si having no protons nearby. However, the silane coupling agent has a $^{1}$H nucleus attributed to an unreacted OH group or organo group nearby and thus has almost no influences.

The Si CP/MAS-NMR spectra of the metal oxide particles surface-treated with the silane coupling agent is classified into spectra of $T^0$, $T^1$, $T^2$, and $T^3$ depending on the crosslinking state of the silane coupling agent. $T^0$, $T^1$, $T^2$, and $T^3$ are chemical structures that are determined by the number of oxygen atoms bonding to two Si's. Specifically, these structures are shown in the following formula (1) and formula (2). In the formula (2), $T^1$, $T^2$, and $T^3$ are shown in succession for easy description. $T^1$ shown in the formula (2) indicates a crosslinking state in which one silicon atom is involved only in one siloxane bond (Si—O—Si). $T^2$ shown in the formula (2) indicates a crosslinking state in which one silicon atom is involved in two siloxane bonds. $T^3$ shown in (2) indicates a crosslinking state in which one silicon atom is involved in three siloxane bonds. $T^0$ shown in the formula (1) indicates a state in which one silicon atom does not have a siloxane bond. In the following formula (1) and formula (2), the H in the OH group may be R. In addition, R represents an alkyl group. In the case of performing a surface treatment of metal oxide particles with a silane coupling agent, since the surface treatment is performed after a hydrolysis/polycondensation reaction, basically, OR groups are not present, and the OH group in the formula (1) and formula (2) are all OH groups. Therefore, as the number decreases like $T^3$, $T^2$, $T^1$, and $T^0$, the number of reaction residues, OH groups, increases and the hydrophilicity of the surface increases.

(1)

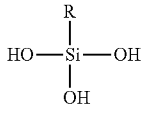

$T^0$ (2)

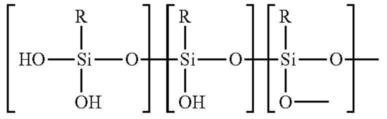

$T^1$ $T^2$ $T^3$

The integral value of the Si CP/MAS-NMR spectra from −30 ppm to −60 ppm is about the sum of the areas of $T^0$, $T^1$, and $T^2$. The integral value from −40 ppm to −50 ppm is the proportion of the area attributed to about $T^1$, and the integral value from −50 ppm to −60 ppm is the proportion of the area attributed to about $T^2$.

The present inventors and the like found that, in the Si CP/MAS-NMR spectrum of the surface-treated metal oxide particles, when the integral value of the spectrum within a measurement range of −30 ppm to −60 ppm is defined as 100, in a case where the value obtained by dividing the integral proportion of the spectrum within a measurement range of −50 ppm to −60 ppm by the integral proportion of the spectrum within a measurement range of −40 ppm to −50 ppm does not satisfy 0.5 or more and 5.0 or less, the ultraviolet shielding property of the surface-treated metal oxide particles deteriorates. In a case where the proportion obtained by dividing the proportion of the area attributed to $T^2$ by the proportion of the area attributed to $T^1$ does not satisfy 0.5 or more and 5.0 or less, the surface-treated metal oxide particles are likely to agglomerate together. In addition, when the above-described proportion is less than 0.5, the ultraviolet shielding property deteriorates, and, when the proportion exceeds 5.0, the rough feeling of the surface-treated metal oxide particles when blended with cosmetics becomes large, which is not preferable.

The reason therefor is presumed as described below.

Generally, cosmetics are used in an oil in water form (W/O form) or a water in oil form (0/W form). In cosmetics containing the surface-treated metal oxide particles for which the value divided by the above-described integral proportion does not satisfy 0.5 or more and 5.0 or less blended with an oil phase, the number of OH groups in the surface-treated metal oxide particles is larger than the optimal number of OH groups. Therefore, in a process of the cosmetics being applied to and dried on the skin, the surface-treated metal oxide particles agglomerate together in the oil phase, which makes it impossible to impart a desired ultraviolet shielding property to the skin.

The present inventors and the like found that, when metal oxide particles are surface-treated with a silane coupling agent such that, in the spectrum measured by the solid-state $^{29}$Si CP/MAS-nuclear magnetic resonance (NMR) spectroscopy, when the integral value of the spectrum within a measurement range of −30 ppm to −60 ppm is defined as 100, the value obtained by dividing the integral proportion of the spectrum within a measurement range of −50 ppm to −60 ppm (the proportion of the area attributed to $T^2$) by the integral proportion of the spectrum within a measurement range of −40 ppm to −50 ppm (the proportion of the area attributed to $T^1$) satisfies 0.5 or more and 5.0 or less, surface-treated metal oxide particles stably exhibiting a high ultraviolet shielding property can be obtained.

In the surface-treated metal oxide particles of the present embodiment, in a case where, in the spectrum measured by the solid-state $^{29}$Si CP/MAS-nuclear magnetic resonance (NMR) spectroscopy, the maximum intensity within the range of −40 ppm to −50 ppm ($T^1$) is defined as a and the maximum intensity within the range of −50 ppm to −60 ppm ($T^2$) is defined as b, a value (a/b) obtained by dividing a by b preferably becomes 1.0 or less. The lower limit value of a/b is not particularly limited and may be 0.3 or more, may be 0.4 or more, may be 0.5 or more, may be 0.6 or more, or may be 0.7 or more.

In the surface-treated metal oxide particles of the present embodiment, in a case where, in the spectrum measured by the solid-state $^{29}$Si CP/MAS-nuclear magnetic resonance (NMR) spectroscopy, the maximum intensity within the range of −20 ppm to −40 ppm ($T^0$) is defined as c and the maximum intensity within the range of −60 ppm to −80 ppm ($T^3$) is defined as d, it is preferable to satisfy b>a>c>d. Such a surface-treated metal oxide particles satisfying such a relationship are excellent in terms of dispersion stability in a composition containing a water-based volatile component and an oil-based component such as a cosmetic. Even when the composition is applied to an object (the skin in the case of a cosmetic), it is possible to exhibit a high ultraviolet shielding property.

According to the surface-treated metal oxide particles of the present embodiment, it is possible to provide particles that are metal oxide particles surface-treated with a silane coupling agent, in which the metal oxide particles have an ultraviolet shielding property, the weight loss of the surface-treated metal oxide particles on drying at 105° C. for 3 hours is 0.5% by mass or less, in the spectrum of the surface-treated metal oxide particles, which is measured by the solid-state $^{29}$Si CP/MAS-nuclear magnetic resonance (NMR) spectroscopy, when the integral value of the spectrum within the measurement range of −30 ppm to −60 ppm is defined as 100, the value obtained by dividing the integral proportion of the spectrum within the measurement range of −50 ppm to −60 ppm by the integral proportion of the spectrum within the measurement range of −40 ppm to −50 ppm is 0.5 or more and 5.0 or less, and the value (D98 (μm)/BET-converted particle diameter (nm)) obtained by dividing the dry particle size D98 (μm) by the BET-converted particle diameter (nm) is 0.01 or more and 5.0 or less. Therefore, surface-treated metal oxide particles that stably exhibit a high ultraviolet shielding property and suppress a rough feeling can be obtained.

(Metal Oxide Particles)

The metal oxide particles that are used as a raw material in the present embodiment, that is, the metal oxide particles before the surface treatment are not particularly limited as long as the particles have an ultraviolet shielding property and can be arbitrarily selected. As the metal oxide particles, for example, zinc oxide particles, titanium oxide particles, cerium oxide particles, and the like can be used. Zinc oxide particles and titanium oxide particles are more preferable as the metal oxide particles since the particles are ordinarily used in cosmetics. Zinc oxide particles are still more preferable due to an excellent ultraviolet shielding property in the UV-A region.

The BET specific surface area of the metal oxide particles in the present embodiment can be arbitrarily selected, but is preferably 1.5 $m^2/g$ or more, more preferably 2.5 $m^2/g$ or more, and still more preferable 4 $m^2/g$ or more. The BET specific surface area of the metal oxide particles is preferably 65 $m^2/g$ or less and more preferably 60 $m^2/g$ or less. If necessary, the BET specific surface area of the metal oxide particles may be 55 $m^2/g$ or less, 50 $m^2/g$ or less, 45 $m^2/g$ or less, 30 $m^2/g$ or less, or 10 $m^2/g$ or less.

The upper limit value and lower limit value of the BET specific surface area of the metal oxide particles can be arbitrarily combined.

When the BET specific surface area of the metal oxide particles is 1.5 $m^2/g$ or more and 65 $m^2/g$ or less, the surface-treated metal oxide particles are excellent in terms of the transparency and the ultraviolet shielding property in the case of being blended with cosmetics.

In a case where there is a desire to enhance the transparency in the case of blending the metal oxide particles with cosmetics, the BET specific surface area of the metal oxide particles is preferably 8 $m^2/g$ or more, more preferably 15 $m^2/g$ or more, and still more preferable 20 $m^2/g$ or more. On the other hand, in a case where there is a desire to enhance the UVA shielding property in the case of blending the metal oxide particles with cosmetics, the BET specific surface area of the metal oxide particles is preferably less than 8 $m^2/g$, more preferably 7.5 $m^2/g$ or less, and still more preferably 7.0 $m^2/g$ or less.

The BET specific surface area of the metal oxide particles in the present embodiment means a value measured by the BET method using a specific surface area-measuring instrument, for example, a full automatic specific surface area-measuring instrument (trade name: Macsorb HM Model-1201 manufactured by Mountech Co., Ltd.).

The average primary particle diameter of the metal oxide particles in the present embodiment can be arbitrarily selected, but is preferably 15 nm or more, and more preferably 20 nm or more. In addition, the average primary particle diameter of the metal oxide particles is preferably 715 nm or less and more preferably 650 nm or less. The average primary particle diameter may be 550 nm or less, 350 nm or less, 250 nm or less, or 180 nm or less as necessary.

When the average primary particle diameter of the metal oxide particles is 15 nm or more and 715 nm or less, the surface-treated metal oxide particles are excellent in terms of the transparency and the ultraviolet shielding property in the case of being blended with cosmetics.

In a case where there is a desire to enhance the transparency in the case of blending the metal oxide particles with cosmetics, the average primary particle diameter of the metal oxide particles is preferably 135 nm or less, more preferably 100 nm or less, and still more preferably 50 nm or less. On the other hand, in a case where there is a desire to enhance the UVA shielding property in the case of blending the metal oxide particles with cosmetics, the primary particle diameter of the metal oxide particles is preferably more than 135 nm, more preferably 140 nm or more, and still more preferably 150 nm or more.

The average primary particle diameter of the metal oxide particles, similar to the BET-converted particle diameter of the surface-treated metal oxide particles, can be calculated from the general formula (2) using the BET specific surface area of the metal oxide particles.

In addition, the average primary particle diameter of the metal oxide particles may be obtained by the following method. That is, in a case where the metal oxide particles are observed using a transmission electron microscope (TEM) or the like, a predetermined number of, for example, 200 or 100, metal oxide particles are selected. In addition, the longest linear portion (maximum major axis) of each of these metal oxide particles is measured, and these measurement values are arithmetically averaged.

In a case where the metal oxide particles agglomerate together, the measurement subject is not the agglomerated particle diameter of this agglomerate. A predetermined number of metal oxide particles (primary particles) that configure this agglomerate are measured and defined as the average primary particle diameter.

In the present embodiment, the BET specific surface area of the surface-treated metal oxide particles tends to become slightly small due to the surface treatment of the metal oxide particles, but is substantially the same magnitude. Similarly, the average primary particle diameter tends to become large due to the surface treatment of the metal oxide particles, but is substantially the same magnitude.

As the metal oxide particles in the present embodiment, high-purity metal oxide particles are preferably used from the viewpoint of improving the dispersion stability in cosmetics.

(Silane Coupling Agent)

The silane coupling agent having an alkoxy group that is used in the present embodiment is not particularly limited as long as the silane coupling agent can be used in cosmetics.

For example, examples of the silane coupling agent include silane coupling agents represented by the following general formula (3) that can be used in cosmetics.

$$R^1Si(OR^2)_3 \quad (3)$$

(Here, $R^1$ represents a phenyl group or an alkyl group or fluoroalkyl group having 1 to 18 carbon atoms, and $R^2$ represents an alkyl group having 1 to 4 carbon atoms.)

Specifically, examples of the silane coupling agent that is used for the surface treatment include alkylalkoxysilane, fluoroalkoxysilane, fluoroalkylalkoxysilane, and the like. Examples thereof also include allylalkoxysilane, polysiloxane having an alkyl group in a side chain, polysiloxane having an allyl group in a side chain, and the like.

Examples of the alkylalkoxysilane include methyltrimethoxysilane, methyltriethoxysilane, methyltripropoxysilane, methyltributoxysilane, ethyltrimethoxysilane, ethyltriethoxysilane, ethyltripropoxysilane, ethyltributoxysilane, n-propyltrimethoxysilane, n-propyltriethoxysilane, n-propyltripropoxysilane, n-propyltributoxysilane, isopropyltrimethoxysilane, isopropyltriethoxysilane, isopropyltripropoxysilane, isopropyltributoxysilane, phenyltrimethoxysilane, phenyltriethoxysilane, phenyltripropoxysilane, phenyltributoxysilane, n-octyltrimethoxysilane, n-octyltriethoxysilane (triethoxycaprylylsilane), n-octadecyltrimethoxysilane, and the like.

Examples of the fluoroalkoxysilane include trifluoropropyltrimethoxysilane, perfluorooctyltriethoxysilane, tridecafluorooctyltriethoxysilane, and the like.

In addition, examples of the silane coupling agent that is used for the surface treatment include polymer-type silane coupling agents having a siloxane skeleton as the main chain and having an alkoxy group and an acrylic group in the molecular structure such as dimethoxydiphenylsilane-triethoxycaprylylsilane crosspolymers, triethoxysilylethyl polydimethylsiloxyethyl dimethicone, and triethoxysilylethyl polydimethylsiloxyethyl hexyl dimethicone and the like.

These silane coupling agents may be used singly or two or more silane coupling agents may be used in combination.

Among the above-described silane coupling agents, a silane coupling agent having an octyl group in the molecule is preferable. Specifically, octyltriethoxysilane, octyltrimethoxysilane, and dimethoxydiphenylsilane-triethoxycaprylylsilane crosspolymers, which have a functional group with approximately moderate polarity and are capable of dealing with oil phases with a wide range of polarity from natural oils or ester oils to silicone oils can be particularly preferably used.

These silane coupling agents may be used singly or two or more silane coupling agents may be used in combination.

The amount of the surface treatment with the silane coupling agent may be appropriately adjusted according to desired characteristics. The amount of the silane coupling agent blended is preferably 2 parts by mass or more and 15 parts by mass or less, more preferably 3 parts by mass or more and 15 parts by mass or less, and still more preferably 4 parts by mass or more and 12 parts by mass or less with respect to 100 parts by mass of the metal oxide particles.

The metal oxide particles are preferably surface-treated with the silane coupling agent in the above-described range since surface-treated particles having excellent dispersibility and an excellent ultraviolet shielding property can be easily obtained. The amount of the silane coupling agent blended may be an amount of the silane coupling agent that is added and used at the time of production.

The metal oxide particles may be surface-treated using, in addition to the silane coupling agent, a surface treatment agent that is used for cosmetics and is not a silane coupling agent to an extent that the characteristics of the surface-treated particles of the present embodiment are not impaired.

As the surface treatment agent that is not a silane coupling agent, for example, an inorganic material such as silica or alumina and an organic material such as a silicone compound, a fatty acid, a fatty acid soap, a fatty acid ester, or an organic titanate compound can be used.

According to the surface-treated metal oxide particles of the present embodiment, surface-treated metal oxide particles that stably exhibit a high ultraviolet shielding property and suppress a rough feeling can be obtained.

[Method for Producing Surface-Treated Metal Oxide Particles]

A method for producing surface-treated metal oxide particles of the present embodiment is not particularly limited and can be arbitrarily selected. The particles can be appropriately produced by a well-known method such as a dry treatment or a wet treatment depending on the component that is used for the surface treatment. As a specific example, metal oxide particles, a silane coupling agent, and, if necessary, a solvent or the like are prepared, these are mixed by a method that is selected as necessary, and the obtained mixture is heated or dried, whereby surface-treated metal oxide particles can be produced.

For example, in the case of a dry treatment, a method in which a surface treatment is performed by the following operation can be exemplified.

First, a silane coupling agent is added by dripping or spraying to and mixed with metal oxide particles as a raw material under stirring in a mixer such as a Henschel mixer or a super mixer. After that, the mixture is strongly stirring at a high speed for a certain period of time. After that, the mixture is heated at a temperature of 70° C. to 200° C. while being continuously stirred. The temperature may be 70° C. to 130° C., 90° C. to 150° C., 130° C. to 170° C., or the like. Next, the mixture is cracked so that a desired D98 of surface-treated metal oxide particles can be obtained in the end. Conditions such as the heating temperature, the stirring time, and the amount of the silane coupling agent can be selected as necessary depending on the material or the silane coupling agent that is used.

For example, in the case of a wet treatment, a method in which a surface treatment is performed by the following method can be exemplified. First, metal oxide particles, a silane coupling agent, and a solvent are mixed at 25° C. to 100° C. for several hours under stirring. After this, the mixture is separated into solid and liquid and cleaned. This obtained cleaned product is heated at 70° C. to 200° C. The temperature may be 70° C. to 130° C., 90° C. to 150° C., 130° C. to 170° C., or the like. Next, the mixture is cracked so that a desired D98 of surface-treated metal oxide particles can be obtained in the end.

In the above-described method by the dry treatment or the wet treatment, water attached to the metal oxide particles may be used as moisture for the hydrolysis of the silane coupling agent. In addition, the moisture for the hydrolysis of the silane coupling agent may be added together with the silane coupling agent or added separately as necessary.

In the above-described method by the dry treatment or the wet treatment, the silane coupling agent may be diluted with a solvent that is miscible with the silane coupling agent before use. Examples of such a solvent include alcohols such as methanol, ethanol, and isopropanol, n-hexane, toluene, xylene, and the like. These solvents may be used singly or two or more solvents may be used in combination. In the case of performing the surface treatment by adding the moisture for the hydrolysis, among these solvents, a polar solvent such as an alcohol that is highly compatible with water is preferably used.

The cracking treatment is not particularly limited as long as each particle can be cracked so that a desired D98 can be obtained in the end. Examples thereof include a method in which each particle is cracked using a crusher. Examples of the crusher include an atomizer, a hammer mill, a jet mill, an impeller mill, a pin mill, and the like.

In the method for producing surface-treated metal oxide particles of the present embodiment, it is possible to suppress the rough feeling of the surface-treated metal oxide particles by performing the cracking treatment so that the D98/BET-converted particle diameter of the surface-treated metal oxide particles that are obtained in the end becomes 0.01 or more and 5.0 or less. As a result, it is possible to improve usability in the case of using the surface-treated metal oxide particles in cosmetics.

The method for producing surface-treated metal oxide particle of the present embodiment includes a step of measuring the metal oxide particles surface-treated with a silane coupling agent having an alkoxy group with a Fourier transform infrared spectrophotometer and determining that a peak derived from the alkoxy group is not detected in a reflection spectrum in 900 $cm^{-1}$ to 1300 $cm^{-1}$ where the surface-treated metal oxide particles are measured (hereinafter, also referred to as "determination step" or "first determination step" in some cases). The method for producing surface-treated metal oxide particles of the present embodiment also preferably includes a step of preparing metal oxide particles surface-treated with a silane coupling agent having an alkoxy group, which is produced by an arbitrarily selected method, a step of measuring these particles with a Fourier transform infrared spectrophotometer, and/or a step of selecting surface-treated metal oxide particles from which a peak containing the alkoxy group is not detected.

By the way, in methods for producing an article, it is quite difficult to produce totally the same articles even when the articles are produced under the same conditions. There is a possibility that the characteristics of the surface-treated metal oxide particles may change depending on a variety of conditions such as a change in the raw material lot, the temperature and humidity on the production date, and the production amount. However, the method for producing surface-treated metal oxide particles of the present embodiment includes the above-described determination step. Therefore, it is possible to quantitatively confirm the amount of unreacted alkoxy groups in the surface-treated particles, and it is possible to easily confirm after production whether or not surface-treated metal oxide particles having an excellent ultraviolet shielding property can be obtained. Therefore, the method for producing surface-treated metal oxide particles of the present embodiment includes the above-described determination step and thereby enables the provision of products with stable quality.

The method for producing surface-treated metal oxide particles of the present embodiment preferably further includes the following step in a case where a peak derived from the alkoxy group is confirmed in the determination step. Specifically, the method for producing surface-treated metal oxide particles of the present embodiment preferably includes a step of heating the metal oxide particles surface-treated with the silane coupling agent having an alkoxy group, that is, the surface-treated metal oxide particles until the peak disappears. The heating conditions in this heating step can be arbitrarily selected. As the heating condition, for example, the temperature may be the same as the temperature during the production of the particles, that is, a temperature of, for example, 70° C. to 200° C. When the method includes this heating step, it is possible to quantitatively manage the amount of unreacted alkoxy groups remaining in the surface-treated particles so as to be in a preferable range. Therefore, surface-treated metal oxide particles having an excellent ultraviolet shielding property can be stably produced.

According to the method for producing surface-treated metal oxide particles of the present embodiment, a step of confirming the presence of residual alkoxy groups is included. Therefore, it is possible to quantitatively confirm the amount of unreacted alkoxy groups, and it is possible to confirm whether or not surface-treated metal oxide particles having an excellent ultraviolet shielding property can be obtained. In addition, the method for producing surface-treated metal oxide particles of the present embodiment may include a heating step. This makes it possible to quantitatively manage the amount of alkoxy groups remaining in the surface-treated particles. Therefore, surface-treated metal oxide particles having an excellent ultraviolet shielding property can be stably produced.

The method for producing surface-treated metal oxide particles of the present embodiment may include a second determination step of determining that the weight loss on drying at 105° C. for 3 hours of the surface-treated metal oxide particle is 0.5% by mass or less.

The second determination step can be performed in the same manner as the above-described method for measuring the weight loss of the surface-treated metal oxide particles on drying at 105° C. for 3 hours.

The second determination step may be performed before or after the determination step in which the Fourier transform infrared spectrophotometer is used.

In a case where the weight loss on drying exceeds 0.5% by mass in the second determination step, the method may include a step of heating the surface-treated metal oxide particles until the weight loss on drying becomes 0.5% by mass or less. The heating conditions in this heating step can be arbitrarily selected. As the heating condition, for example, the temperature may be the same as the temperature during the production of the particles, that is, a temperature of, for example, 70° C. to 200° C.

The method for producing surface-treated metal oxide particles of the present embodiment preferably includes a step of heating the surface-treated metal oxide particles until the peak derived from the alkoxy group is not detected in the first determination step and the weight loss on drying becomes 0.5% by mass or less in the second determination step.

In addition, in a case where desired characteristics are not satisfied in at least one of the first determination step and the second determination step, it is preferable to heat the surface-treated metal oxide particles at the same temperature as the temperature during the production of the particles, for example, a temperature of 70° C. to 200° C. until such characteristics are satisfied (heating step).

The method for producing surface-treated metal oxide particles of the present embodiment may include a third step of determining whether or not, in the spectrum of the metal oxide particles surface-treated with the silane coupling agent measured by the solid-state $^{29}$Si CP/MAS-nuclear magnetic resonance (NMR) spectroscopy, the value obtained by dividing the integral proportion of the spectrum within the measurement range of −50 ppm to −60 ppm by the integral proportion of the spectrum within the measurement range of −40 ppm to −50 ppm satisfies 0.5 or more and 5.0 or less.

In a case where the value does not satisfy 0.5 or more and 5.0 or less, the method preferably includes a step of heating the mixture of the silane coupling agent and the metal oxide particles. In this case, it is preferable to heat the mixture at an arbitrarily selected temperature, for example, a temperature of 70° C. to 200° C. until the characteristic is satisfied.

When the method includes this step, since the amount of OH groups in the surface-treated particles can be quantitatively managed, it is possible to stably produce surface-treated metal oxide particles having an excellent ultraviolet shielding property.

In addition, the method for producing surface-treated metal oxide particles of the present embodiment may include a step of determining whether or not the surface-treated metal oxide particles satisfies that the value (D98 (μm)/BET-converted particle diameter (nm)) obtained by dividing the dry particle size D98 (μm) by the BET-converted particle diameter (nm) is 0.01 or more and 5.0 or less.

In addition, as described above, the method for producing surface-treated metal oxide particles of the present embodiment may include a step of confirming the ultraviolet shielding property of the surface-treated metal oxide particles.

[Dispersion Liquid]

A dispersion liquid of the present embodiment contains the surface-treated metal oxide particles of the present embodiment and a dispersion medium.

The dispersion liquid of the present embodiment also contains a paste-form dispersing element having a high viscosity.

The dispersion medium is not particularly limited as long as the dispersion medium can be formulated in cosmetics and allows the surface-treated particles to be dispersed.

As the dispersion medium, for example, water, alcohols, esters, ethers, natural oils, ester oils, silicone oils, and the like are preferably used.

Examples of the alcohol include methanol, ethanol, n-propanol, isopropanol, n-butanol, 2-butanol, octanol, glycerin, and the like.

Examples of the ester include ethyl acetate, butyl acetate, ethyl lactate, propylene glycol monomethyl ether acetate, propylene glycol monoethyl ether acetate, γ-butyrolactone, and the like.

Examples of the ether include diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, diethylene glycol monoethyl ether, and the like.

In addition, as other dispersion media, ketones, aromatic hydrocarbons, cyclic hydrocarbons, amides, chain polysiloxanes, cyclic polysiloxanes, denatured polysiloxanes, hydrocarbon oils, ester oils, silicone oils, higher fatty acids, higher alcohols, and the like can be used.

Examples of the ketones include acetone, methyl ethyl ketone, methyl isobutyl ketone, acetyl acetone, cyclohexanone, and the like.

Examples of the aromatic hydrocarbons include benzene, toluene, xylene, ethyl benzene, and the like.

Examples of the cyclic hydrocarbons include cyclohexane and the like.

Examples of the amides include dimethylformamide, N,N-dimethylacetoacetamide, N-methylpyrrolidone, and the like.

Examples of the chain-like polysiloxanes include dimethyl polysiloxane, methyl phenyl polysiloxane, diphenyl polysiloxane, and the like.

Examples of the cyclic polysiloxanes include octamethyl cyclotetrasiloxane, decamethylcyclopentasiloxane, dodecamethyl cyclohexasiloxane, and the like.

Examples of the denatured polysiloxanes include amino-denatured polysiloxane, polyether-denatured polysiloxane, alkyl-denatured polysiloxane, fluorine-denatured polysiloxane, and the like.

Examples of the hydrocarbon oils include liquid paraffin, squalane, isoparaffin, branched chain-line light paraffin, petrolatum, ceresin, and the like.

Examples of the ester oils include isopropyl myristate, cetyl isooctanoate, glyceryl trioctanoate, and the like.

Examples of the silicone oils include decamethylcyclopentasiloxane, dimethylpolysiloxane, methylphenylpolysiloxane, and the like.

Examples of the higher fatty acids include lauric acid, myristic acid, palmitic acid, stearic acid, and the like.

Examples of the higher alcohols include lauryl alcohol, cetyl alcohol, stearyl alcohol, hexyl dodecanol, isostearyl alcohol, and the like.

These dispersion media may be used singly or two or more dispersion media may be used in combination.

The dispersion liquid of the present embodiment may contain an ordinarily used additive to an extent that the characteristics thereof are not impaired.

As the additive, for example, a preservative, a dispersant, a dispersion aid, a stabilizer, a water-soluble binder, a viscosity improver, an oil-soluble chemical, oil-soluble pigments, oil-soluble proteins, an UV absorber, and the like are preferably used.

The particle size (d50) of the surface-treated metal oxide particles when the cumulative volume percentage of the particle size distribution in the dispersion liquid of the present embodiment is 50% can be arbitrarily selected, but is preferably 300 nm or less, more preferably 250 nm or less, and still more preferably 200 nm or less.

The lower limit value of d50 is not particularly limited and may be, for example, 50 nm or more, may be 100 nm or more, or may be 150 nm or more. The upper limit value and lower limit value of d50 can be arbitrarily combined together.

In addition, the particle size (d90) of the surface-treated metal oxide particles when the cumulative volume percentage of the particle size distribution in the dispersion liquid of the present embodiment is 90% can be arbitrarily selected, but is preferably 400 nm or less, more preferably 350 nm or less, and still more preferably 300 nm or less.

The lower limit value of d90 is not particularly limited and may be, for example, 100 nm or more, may be 150 nm or more, or may be 200 nm or more. The upper limit value and lower limit value of d90 can be arbitrarily combined together.

In a case where d50 of the dispersion liquid is 300 nm or less, when a cosmetic produced using this dispersion liquid has been applied to the skin, it is easy to uniformly distribute the surface-treated particles and an ultraviolet shielding effect improves, which is preferable. In addition, in a case where d90 of the dispersion liquid is 400 nm or less, the transparency of the dispersion liquid is high, and the transparency of cosmetics produced using this dispersion liquid also becomes high, which is preferable.

That is, when d50 and d90 in the dispersion liquid of the present embodiment are within the above-described ranges, it is possible to obtain a dispersion liquid having excellent transparency and an excellent ultraviolet shielding property. In addition, cosmetics produced using this dispersion liquid are also excellent in terms of transparency and an ultraviolet shielding property.

The cumulative volume percentage of the particle size distribution in the dispersion liquid can be measured using a dynamic light scattering type particle size distribution-measuring instrument.

The content of the surface-treated metal oxide particles in the dispersion liquid of the present embodiment needs to be appropriately adjusted according to desired characteristics.

In the case of using the dispersion liquid of the present embodiment in a cosmetic, the content of the surface-treated metal oxide particles in the dispersion liquid can be arbitrarily selected, and is preferably 10% by mass or more, more preferably 20% by mass or more, and still more preferably 30% by mass or more. In addition, the content of the surface-treated metal oxide particles in the dispersion liquid is preferably 90% by mass or less, more preferably 85% by mass or less, and still more preferably 80% by mass or less. The upper limit value and lower limit value of the content of the surface-treated metal oxide particles in the dispersion liquid can be arbitrarily combined together.

When the content of the surface-treated metal oxide particles in the dispersion liquid is within the above-described range, the surface-treated metal oxide particles are contained at a high concentration. This makes it possible to improve the degree of freedom of formulation and makes it possible to adjust the viscosity of the dispersion liquid such that the dispersion liquid is easily handled.

The viscosity of the dispersion liquid of the present embodiment can be arbitrarily selected, and is preferably 5 Pas or more, more preferably 8 Pas or more, still more preferably 10 Pas or more, and most preferably 15 Pas or more. In addition, the viscosity of the dispersion liquid is preferably 300 Pas or less, more preferably 100 Pas or less, still more preferably 80 Pas or less, and most preferably 60 Pas or less. The upper limit value and lower limit value of the viscosity of the dispersion liquid can be arbitrarily combined together.

When the viscosity of the dispersion liquid is within the above-described range, it is possible to obtain a dispersion liquid that is easy to handle even when the dispersion liquid contains a solid content (surface-treated metal oxide particles) at a high concentration.

Regarding the dispersion liquid of the present embodiment, in a case where the dispersion liquid containing 10% by mass of the surface-treated particles is applied onto a predetermined substrate such that the thickness after drying becomes 12 μm and naturally drying for 15 minutes to form a coated film, physical property values that are measured from the coated film are preferably within the following ranges.

That is, the transmittance of the coated film at 450 nm is preferably 40% or higher, more preferably 45% or higher, and still more preferably 50% or higher. The upper limit value of the transmittance is not particularly limited and may be 100% or lower, may be 90% or lower, or may be 80% or lower. The upper limit value and lower limit value of the transmittance of the coated film at 450 nm can be arbitrarily combined together.

As the transmittance of the coated film at 450 nm increases, the transparency becomes superior. Therefore, the transmittance at 450 nm is preferably high.

In addition, the average transmittance of the coated film at 290 nm to 320 nm is preferably 10% or lower, more preferably 7% or lower, and still more preferably 5% or lower. The lower limit value is not particularly limited and may be 0% or higher, may be 0.5% or higher, or may be 1% or higher. The upper limit value and lower limit value of the average transmittance of the coated film at 290 nm to 320 nm can be arbitrarily combined together.

As the average transmittance of the coated film at 290 nm to 320 nm decreases, the ultraviolet shielding property becomes superior. Therefore, the average transmittance at 290 nm to 320 nm is preferably small.

In addition, the SPF value of the coated film is preferably 30 or higher, more preferably 35 or higher, and still more preferably 40 or higher. The upper limit value of the SPF value of the coated film is not particularly limited and may be 150 or lower, may be 100 or lower, or may be 80 or lower. The upper limit value and lower limit value of the SPF value of the coated film can be arbitrarily combined together.

As the SPF value of the coated film increases, an effect of preventing ultraviolet B waves becomes stronger. Therefore, the SPF value is preferably large.

The critical wavelength of the coated film is preferably 370 nm or more. When the critical wavelength of the coated film is 370 nm or more, the coated film is capable of shielding a wide range of ultraviolet rays such as long wavelength ultraviolet rays (UVA) and short wavelength ultraviolet rays (UVB). Therefore, cosmetics containing the dispersion liquid of the present embodiment has a critical wavelength of 370 nm or more, and films formed on the skin by the cosmetics are capable of shielding a wide range of ultraviolet rays such as long wavelength ultraviolet rays (UVA) and short wavelength ultraviolet rays (UVB).

In the present specification, the "critical wavelength" is a value that is obtained by measuring the coated film formed by the application of the dispersion liquid. Specifically, for the coated film, the absorption spectrum in an ultraviolet region of 290 nm or more and 400 nm or less is measured, and the obtained absorption spectrum is integrated from 290 nm toward the long wavelength side. At this time, the wavelength at which the integral area becomes 90% of the integral area in the entire region of 290 nm or more and 400 nm or less is defined as the "critical wavelength" that is sought.

A method for producing the dispersion liquid of the present embodiment is not particularly limited. Examples thereof include a method in which the surface-treated particles of the present embodiment and a dispersion medium are mechanically dispersed with a well-known dispersion apparatus.

The dispersion apparatus can be selected as necessary, and examples thereof include a stirrer, a planetary mixer, a homogenizer, an ultrasonic homogenizer, a sand mill, a ball mill, a roll mill, and the like.

The dispersion liquid of the present embodiment can be used for, in addition to cosmetics, paints and the like having an ultraviolet shielding function, a gas transmission-suppressing function, or the like.

The dispersion liquid of the present embodiment contains the surface-treated metal oxide particles of the present embodiment and is thus capable of stably exhibiting a high ultraviolet shielding property.

[Composition]

A composition of the present embodiment contains the surface-treated particles of the present embodiment and a polymer.

The content of the surface-treated particles in the composition of the present embodiment may be appropriately adjusted according to desired characteristics. The content is, for example, preferably 10% by mass or more and 40% by mass or less and more preferably 20% by mass or more and 30% by mass or less.

When the content of the surface-treated particles in the composition is within the above-described range, since the solid content (surface-treated metal oxide particles) is contained at a high concentration, the characteristics of the surface-treated particles can be sufficiently obtained, and it is possible to obtain a composition in which the surface-treated particles are uniformly dispersed.

The polymer in the composition of the present embodiment is not particularly limited, and, for example, a water-soluble polymer, a semi-synthetic polymer, a synthetic polymer, a resin, or the like can be used.

Examples of the water-soluble polymer include gelatin, casein, collagen, hyaluronic acid, albumin, starch, and the like.

Examples of the semi-synthetic polymer include methyl cellulose, ethyl cellulose, methyl hydroxypropyl cellulose, carboxymethyl cellulose, hydroxymethyl cellulose, hydroxypropyl cellulose, sodium carboxymethyl cellulose, propylene glycol alginic acid ester, and the like.

Examples of the synthetic polymer include polyvinyl alcohol, polyvinylpyrrolidone, carbomer (carboxyvinyl polymer), polyacrylic acid salt, polyethylene oxide, and the like.

The resin is not particularly limited as long as the resin is ordinarily used for industrial applications, and examples thereof include an acrylic resin, an epoxy resin, a urethane resin, a polyester resin, a silicone resin, and the like. In the case of being used for a cosmetic application, a silicone resin is preferably used.

The content of the polymer in the composition of the present embodiment is not particularly limited and is appropriately adjusted depending on the intended characteristics of the composition.

The composition of the present embodiment may contain a dispersion medium.

The dispersion medium is not particularly limited as long as the dispersion medium is ordinarily used for industrial applications, and examples thereof include water, alcohols such as methanol, ethanol, and propanol, methyl acetate, ethyl acetate, toluene, methyl ethyl ketone, methyl isobutyl ketone, and the like. These dispersion media may be used singly or two or more dispersion media may be used in combination.

The content of the dispersion medium in the composition of the present embodiment is not particularly limited and is appropriately adjusted depending on the intended characteristics of the composition.

The composition of the present embodiment may contain an ordinarily used additive to an extent that the characteristics thereof are not impaired.

Examples of the additive include a polymerization initiator, a dispersant, a preservative, a viscosity improver, a higher fatty acid, and the like.

A method for producing the composition of the present embodiment is not particularly limited, and examples thereof include a method in which the surface-treated particles of the present embodiment and the polymer are mechanically mixed together with a well-known mixing apparatus.

In addition, there is another method in which the above-described dispersion liquid and the polymer are mechanically mixed together with a well-known mixing apparatus.

Examples of the mixing apparatus include a stirrer, a planetary mixer, a homogenizer, an ultrasonic homogenizer, and the like.

A coated film can be formed by applying the composition of the present embodiment to an arbitrarily selected base material, for example, a plastic base material such as a polyester film using an ordinary application method such as a roll coating method, a flow coating method, a spray coating method, a screen printing method, a brush coating method, or an immersion method. These coated films can be utilized for an arbitrarily selected application, for example, an ultraviolet shielding film or a gas barrier film.

The composition of the present embodiment contains the surface-treated metal oxide particles of the present embodiment and is thus capable of stably exhibiting a high ultraviolet shielding property.

[Cosmetic]

A cosmetic of an embodiment of the present embodiment contains at least one selected from the group consisting of the surface-treated metal oxide particles of the present embodiment, the dispersion liquid of the present embodiment, and the composition of the present embodiment.

A cosmetic of another embodiment of the present embodiment contains a cosmetic base raw material and at least one selected from the group consisting of the surface-treated metal oxide particles of the present embodiment, the dispersion liquid of the present embodiment, and the composition of the present embodiment.

The cosmetic base raw material is a variety of raw materials that form the main body of a cosmetic product. Examples of the cosmetic base raw material include an oily raw material, an aqueous raw material, a surfactant, a powder raw material, and the like.

The oily raw material can be arbitrarily selected, and examples thereof include fats and oils, higher fatty acids, higher alcohols, ester oils, and the like.

The aqueous raw material can be arbitrarily selected, and examples thereof include purified water, alcohol, a viscosity improver, and the like.

The powder raw material can be arbitrarily selected, and examples thereof include a colored pigment, a white pigment, a pearl agent, an extender pigment, and the like.

The cosmetic of the present embodiment can be obtained by, for example, blending the dispersion liquid of the present embodiment with the cosmetic base raw material such as an emulsion, a cream, a foundation, a lip stick, a blush, or an eye shadow as in the related art.

In addition, the cosmetic of the present embodiment can be obtained by, for example, blending the surface-treated particles of the present embodiment with an oil phase or a water phase to form an O/W form or W/O form emulsion and then blending the emulsion with the cosmetic base raw material.

The content of the surface-treated metal oxide particles in the cosmetic of the present embodiment needs to be appropriately adjusted according to desired characteristics. For example, the lower limit value of the content of the surface-treated particles may be 0.01% by mass or more, may be 0.1% by mass or more, or may be 1% by mass or more. In addition, the upper limit value of the content of the surface-treated particles may be 50% by mass or less, may be 40% by mass or less, or may be 30% by mass or less. The upper limit value and lower limit value of the content of the surface-treated particles in the cosmetic can be arbitrarily combined together.

Hereinafter, a sunscreen cosmetic will be specifically described.

In the sunscreen cosmetic, the content of the surface-treated metal oxide particles is also preferably adjusted in order to effectively shield ultraviolet rays, particularly, long wavelength ultraviolet rays (UVA) and to obtain favorable usability with a few powdery squeak. For example, the lower limit value of the content of the surface-treated metal oxide particles in the sunscreen cosmetic is preferably 0.01% by mass or more, more preferably 0.1% by mass or more, and still more preferably 1% by mass or more. In addition, the upper limit value of the content of the surface-treated particles in the sunscreen cosmetic may be 50% by mass or less, may be 40% by mass or less, or may be 30% by mass or less. The upper limit value and lower limit value of the content of the surface-treated particles in the sunscreen cosmetic can be arbitrarily combined together.

In addition, within the above-described range, a preferable range such as 5% by mass to 15% by mass or 10% by mass to 20% by mass can be arbitrarily selected.

The sunscreen cosmetic may contain a hydrophobic dispersion medium, inorganic fine particles or an inorganic pigment other than the surface-treated metal oxide particles, a hydrophilic dispersion medium, oil and fat, a surfactant, a moisturizing agent, a viscosity improver, a pH adjuster, a nutritional supplement, an antioxidant, a perfume, and the like as necessary.

Examples of the hydrophobic dispersion medium include hydrocarbon oils, ester oils, silicone oils, higher fatty acids, higher alcohols, and the like.

Examples of the hydrocarbon oils include liquid paraffin, squalane, isoparaffin, branched chain-line light paraffin, petrolatum, ceresin, and the like.

Examples of the ester oils include isopropyl myristate, cetyl isooctanoate, glyceryl trioctanoate, and the like.

Examples of the silicone oils include decamethylcyclopentasiloxane, dimethylpolysiloxane, methylphenylpolysiloxane, and the like.

Examples of the higher fatty acids include lauric acid, myristic acid, palmitic acid, stearic acid, and the like.

Examples of the higher alcohols include lauryl alcohol, cetyl alcohol, stearyl alcohol, hexyl dodecanol, isostearyl alcohol, and the like.

Examples of the inorganic fine particles or inorganic pigment other than the surface-treated metal oxide particles that is contained in the cosmetic include calcium carbonate, calcium phosphate (apatite), magnesium carbonate, calcium silicate, magnesium silicate, aluminum silicate, kaolin, talc, titanium oxide, aluminum oxide, yellow oxide of iron, γ-iron oxide, cobalt titanate, cobalt violet, silicon oxide, and the like.

The sunscreen cosmetic may further contain at least one organic ultraviolet absorber.

Examples of the organic ultraviolet absorber include a benzotriazole-based ultraviolet absorber, a benzoyl methane-based ultraviolet absorber, a benzoic acid-based ultraviolet absorber, an anthranilic acid-based ultraviolet absorber, a salicylic acid-based ultraviolet absorber, a cinnamic acid-based ultraviolet absorber, a silicone-based cinnamic acid ultraviolet absorber, organic ultraviolet absorbers other than the above-described ultraviolet absorbers, and the like.

Examples of the benzotriazole-based ultraviolet absorber include 2,2'-hydroxy-5-methylphenylbenzotriazole, 2-(2'-hydroxy-5'-t-octylphenyl)benzotriazole, 2-(2'-hydroxy-5'-methylphenyl)benzotriazole, and the like.

Examples of the benzoyl methane-based ultraviolet absorber include dibenzalazine, dianisoylmethane, 4-tert-butyl-4'-methoxydibenzoylmethane, 1-(4'-isopropylphenyl)-3-phenyl propane-1,3-dione, 5-(3,3'-dimethyl-2-norbornylidene)-3-pentane-2-one, and the like.

Examples of the benzoic acid-based ultraviolet absorber include para-aminobenzoic acid (PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA methyl ester, and the like.

Examples of the anthranilic acid-based ultraviolet absorber include homo menthyl-N-acetyl anthranilate and the like.

Examples of the salicylic acid-based ultraviolet absorber include amyl salicylate, menthyl salicylate, homo menthyl salicylate, octyl salicylate, phenyl salicylate, benzyl salicylate, p-2-propanol phenyl salicylate, and the like.

Examples of the cinnamic acid-based ultraviolet absorber include octyl methoxycinnamate (ethylhexyl methoxycinnamate), di-para methoxy cinnamate-mono-2-glyceryl ethylhexanoate, octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate(2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethylhexanoyl-diparamethoxy cinnamate, and the like.

Examples of the silicone-based cinnamic acid ultraviolet absorber include [3-bis(trimethylsiloxy)methylsilyl-1-methylpropyl]-3,4,5-trimethoxy cinnamate, [3-bis(trimethylsiloxy)methylsilyl-3-methylpropyl]-3,4,5-trimethoxy cinnamate, [3-bis(trimethylsiloxy)methylsilylpropyl]-3,4,5-trimethoxy cinnamate, [3-bis(trimethylsiloxy) methylsilylbutyl]-3,4,5-trimethoxy cinnamate, [3-tris (trimethylsiloxy)silylbutyl]-3,4,5-trimethoxy cinnamate, [3-tris(trimethylsiloxy)silyl-1-methylpropyl]-3,4-dimethoxy cinnamate, and the like.

Examples of the organic ultraviolet absorbers other than the above-described ultraviolet absorbers include 3-(4'-methylbenzyliene)-d,l-camphor, 3-benzylidene-d,l-camphor, urocanic acid, ethyl urocanate esters, 2-phenyl-5-methylbenzoxane, 5-(3,3'-dimethyl-2-norbornylidene)-3-pentane-2-one, silicone-denatured ultraviolet absorbers, fluorine-denatured ultraviolet absorbers, and the like. These ultraviolet absorbers may be used singly or two or more ultraviolet absorbers may be used in combination.

The critical wavelength of the cosmetic of the present embodiment is preferably 370 nm or more. When the critical wavelength of the cosmetic is 370 nm or more, the cosmetic is capable of shielding a wide range of ultraviolet rays such as long wavelength ultraviolet rays (UVA) and short wavelength ultraviolet rays (UVB).

The cosmetic of the present embodiment contains at least one selected from the group consisting of the surface-treated metal oxide particles of the present embodiment, the dispersion liquid of the present embodiment, and the composition of the present embodiment. Therefore, the cosmetic stably exhibits a high ultraviolet shielding property.

EXAMPLES

Hereinafter, the present invention will be more specifically described with examples and comparative examples, but the present invention is not limited to the following examples.

Example 1

"Production of Surface-Treated Metal Oxide Particles"

A liquid mixture of 100 parts by mass of zinc oxide particles (BET specific surface area: 30 $m^2/g$, manufactured by Sumitomo Osaka Cement Co., Ltd.), 8 parts by mass of octyltriethoxysilane (trade name: KBE-3083, manufactured by Shin-Etsu Chemical Co., Ltd.), 0.6 parts by mass of pure water, and 34.2 parts by mass of isopropyl alcohol was mixed in a Henschel mixer.

Next, the liquid mixture was dried at 80° C. until the isopropyl alcohol was removed.

Next, the obtained dried product was cracked by 16000 times of rotation with a hammer mill until D98 became 500 μm or less, and this cracked powder was dried at 120° C. for 3 hours, thereby obtaining surface-treated zinc oxide particles of Example 1.

The particles were evaluated by a method to be described below. The BET specific surface area of the obtained surface-treated zinc oxide particles was 25 $m^2/g$, and D98 was 30 μm. The weight loss on drying at 105° C. for 3 hours of the obtained surface-treated zinc oxide particles was 0.10% by mass.

D98 of the surface-treated zinc oxide particles was the same before and after the drying at 120° C. for 3 hours.

"Production of Dispersion Liquid"

10 Parts by mass of the surface-treated zinc oxide particles of Example 1, 2 parts by mass of PEG-9 polydimethylsiloxyethyl dimethicone (trade name: KF-6028, manufactured by Shin-Etsu Chemical Co., Ltd.), and 88 parts by mass of decamethylcyclopentasiloxane (trade name: SH245, manufactured by Dow Toray Co., Ltd.) were stirred at 4000 rpm using a stirrer, thereby obtaining a dispersion liquid of Example 1.

The dispersion liquid was evaluated by a method to be described below. The evaluation results are shown in Table 1.

PEG-9 polydimethylsiloxyethyl dimethicone is added to the mixture as a dispersant for dispersing the surface-treated zinc oxide particles in decamethylcyclopentasiloxane.

Example 2

Surface-treated zinc oxide particles of Example 2 were obtained in the same manner as in Example 1 except that, in Example 1, the cracked powder was dried at 120° C. for 2 hours instead of being dried at 120° C. for 3 hours.

A dispersion liquid of Example 2 was obtained in the same manner as in Example 1 except that the surface-treated zinc oxide particles of Example 2 were used instead of the surface-treated zinc oxide particles obtained in Example 1.

The evaluation results of the particles and the dispersion liquid are shown in Table 1.

Example 3

Surface-treated zinc oxide particles of Example 3 were obtained in the same manner as in Example 1 except that, in Example 1, zinc oxide particles having a BET specific surface area of 45 $m^2/g$ were used instead of the zinc oxide particles having a BET specific surface area of 30 $m^2/g$.

A dispersion liquid of Example 3 was obtained in the same manner as in Example 1 except that the surface-treated zinc oxide particles of Example 3 were used instead of the surface-treated zinc oxide particles obtained in Example 1.

The evaluation results of the particles and the dispersion liquid are shown in Table 1.

Example 4

Surface-treated zinc oxide particles of Example 4 were obtained in the same manner as in Example 1 except that, in Example 1, the cracked powder was dried at 120° C. for 2 hours instead of being dried at 120° C. for 3 hours and zinc oxide particles having a BET specific surface area of 45 $m^2/g$ were used instead of the zinc oxide particles having a BET specific surface area of 30 $m^2/g$.

A dispersion liquid of Example 4 was obtained in the same manner as in Example 1 except that the surface-treated zinc oxide particles of Example 4 were used instead of the surface-treated zinc oxide particles obtained in Example 1.

The evaluation results of the particles and the dispersion liquid are shown in Table 1.

Example 5

A liquid mixture of 100 parts by mass of zinc oxide particles (BET specific surface area: 60 $m^2/g$, manufactured by Sumitomo Osaka Cement Co., Ltd.), 12 parts by mass of octyltriethoxysilane (trade name: KBE-3083, manufactured by Shin-Etsu Chemical Co., Ltd.), 0.6 parts by mass of pure water, and 34.2 parts by mass of isopropyl alcohol was mixed in a Henschel mixer.

Next, the liquid mixture was dried at 80° C. until the isopropyl alcohol was removed.

Next, the obtained dried product was cracked by 16000 times of rotation with a hammer mill until D98 became 500

μm or less, and this cracked powder was dried at 120° C. for 3 hours, thereby obtaining surface-treated zinc oxide particles of Example 5.

A dispersion liquid of Example 5 was obtained in the same manner as in Example 1 except that the surface-treated zinc oxide particles of Example 5 were used instead of the surface-treated zinc oxide particles obtained in Example 1.

The evaluation results of the particles and the dispersion liquid are shown in Table 1.

Example 6

A liquid mixture of 100 parts by mass of zinc oxide particles (BET specific surface area: 20 $m^2/g$, manufactured by Sumitomo Osaka Cement Co., Ltd.), 6 parts by mass of octyltriethoxysilane (trade name: KBE-3083, manufactured by Shin-Etsu Chemical Co., Ltd.), 0.6 parts by mass of pure water, and 34.2 parts by mass of isopropyl alcohol was mixed in a Henschel mixer.

Next, the liquid mixture was dried at 80° C. until the isopropyl alcohol was removed.

Next, the obtained dried product was cracked by 16000 times of rotation with a hammer mill until D98 became 500 μm or less, and this cracked powder was dried at 120° C. for 3 hours, thereby obtaining surface-treated zinc oxide particles of Example 6.

A dispersion liquid of Example 6 was obtained in the same manner as in Example 1 except that the surface-treated zinc oxide particles of Example 6 were used instead of the surface-treated zinc oxide particles obtained in Example 1.

The evaluation results of the particles and the dispersion liquid are shown in Table 1.

Example 7

A liquid mixture of 100 parts by mass of zinc oxide particles (BET specific surface area: 8 $m^2/g$, manufactured by Sumitomo Osaka Cement Co., Ltd.), 6 parts by mass of octyltriethoxysilane (trade name: KBE-3083, manufactured by Shin-Etsu Chemical Co., Ltd.), 0.6 parts by mass of pure water, and 34.2 parts by mass of isopropyl alcohol was mixed in a Henschel mixer.

Next, the liquid mixture was dried at 80° C. until the isopropyl alcohol was removed.

Next, the obtained dried product was cracked by 16000 times of rotation with a hammer mill until D98 became 500 μm or less, and this cracked powder was dried at 120° C. for 3 hours, thereby obtaining surface-treated zinc oxide particles of Example 7.

A dispersion liquid of Example 7 was obtained in the same manner as in Example 1 except that the surface-treated zinc oxide particles of Example 7 were used instead of the surface-treated zinc oxide particles obtained in Example 1.

The evaluation results of the particles and the dispersion liquid are shown in Table 1.

Comparative Example 1

Surface-treated zinc oxide particles of Comparative Example 1 were obtained in the same manner as in Example 1 except that, in Example 1, the cracked powder was dried at 100° C. for 1 hour instead of being dried at 120° C. for 3 hours.

A dispersion liquid of Comparative Example 1 was obtained in the same manner as in Example 1 except that the surface-treated zinc oxide particles of Comparative Example 1 were used instead of the surface-treated zinc oxide particles obtained in Example 1.

The BET specific surface area of the obtained surface-treated zinc oxide particles was 25 $m^2/g$, and D98 was 60 μm. The weight loss on drying at 105° C. for 3 hours of the obtained surface-treated zinc oxide particles was 0.60% by mass.

The evaluation results of the particles and the dispersion liquid are shown in Table 1.

Comparative Example 2

A liquid mixture of 100 parts by mass of zinc oxide particles (BET specific surface area: 45 $m^2/g$, manufactured by Sumitomo Osaka Cement Co., Ltd.), 8 parts by mass of octyltriethoxysilane (trade name: KBE-3083, manufactured by Shin-Etsu Chemical Co., Ltd.), 0.6 parts by mass of pure water, and 34.2 parts by mass of isopropyl alcohol was mixed in a Henschel mixer.

Next, the liquid mixture was dried at 80° C. until the isopropyl alcohol was removed.

Next, the obtained dried product was cracked by 8000 times of rotation with a hammer mill until D98 became 700 μm or less, and this cracked powder was dried at 120° C. for 3 hours, thereby obtaining surface-treated zinc oxide particles of Comparative Example 2.

A dispersion liquid of Comparative Example 2 was obtained in the same manner as in Example 1 except that the surface-treated zinc oxide particles of Comparative Example 2 were used instead of the surface-treated zinc oxide particles obtained in Example 1.

The evaluation results of the particles and the dispersion liquid are shown in Table 1.

"Evaluation"

(Measurement with Fourier Transform Infrared Spectrophotometer (FT-IR))

For the surface-treated zinc oxide particles obtained in Example 1 to Example 7, Comparative Example 1, and Comparative Example 2, the spectra from 600 $cm^{-1}$ to 1500 $cm^{-1}$ were measured by the ATR method using a Fourier transform infrared spectrophotometer FT/IR670Plus (manufactured by JASCO Corporation). In addition, as a reference example, the spectrum of octyltriethoxysilane was measured.

As a result, from the surface-treated zinc oxide particles obtained in Example 1 to Example 7 and Comparative Example 2, peaks were not detected at 1170 $cm^{-1}$. 1100 $cm^{-1}$, 1080 $cm^{-1}$, and 950 $cm^{-1}$. In contrast, from the surface-treated zinc oxide particles of Comparative Example 1, peaks were detected at 1170 $cm^{-1}$, 1100 $cm^{-1}$, 1080 $cm^{-1}$, and 950 $cm^{-1}$. That is, it was confirmed that unreacted octyltriethoxysilane was not detected on the particle surfaces in Example 1 to Example 7 and Comparative Example 2 and unreacted octyltriethoxysilane remained in Comparative Example 1. In Table 1, "Present" was displayed in a case where a peak was detected, and "Absent" was displayed in a case where a peak was not detected.

FIG. 1 shows the measurement results with FT-IR of Example 1, Comparative Example 1, and octyltriethoxysilane.

(Measurement of Weight Loss on Drying)

2 g of each of the surface-treated zinc oxide particles obtained in Example 1 to Example 7, Comparative Example 1, and Comparative Example 2 was heated in a dryer set to 105° C. for 3 hours. The masses before and after heating were measured, and the mass reduction rate was obtained and regarded as the weight loss on drying (% by mass). That is, a value that was obtained from the following formula (1) was regarded as the weight loss on drying. The results are shown in Table 1.

Weight loss on drying (% by mass) of surface-treated metal oxide particles=(mass of surface-treated metal oxide particles before heating−mass of surface-treated metal oxide particles after heating)/mass of surface-treated metal oxide particles before heating×100 (1)

(Measurement of Particle Size Distribution)

Regarding D98 of the surface-treated zinc oxide particles obtained in Example 1 to Example 7, Comparative Example 1, and Comparative Example 2, the volume particle size distributions were measured in a dry manner using a laser diffraction-type particle size distribution-measuring instrument (Model No.: Mastersizer 3000, manufactured by Malvern Panalytical Ltd.). The results are shown in Table 1.

(Measurement of BET Specific Surface Area)

The BET specific surface areas of the surface-treated zinc oxide particles obtained in Example 1 to Example 7, Comparative Example 1, and Comparative Example 2 were measured by the BET method using a full automatic specific surface area-measuring instrument (trade name: Macsorb HM Model-1201 manufactured by Mountech Co., Ltd.). The results are shown in Table 1.

In addition, the BET-converted particle diameter calculated from the formula (2) are shown in Table 1.

(Measurement of NMR)

Figure 2:
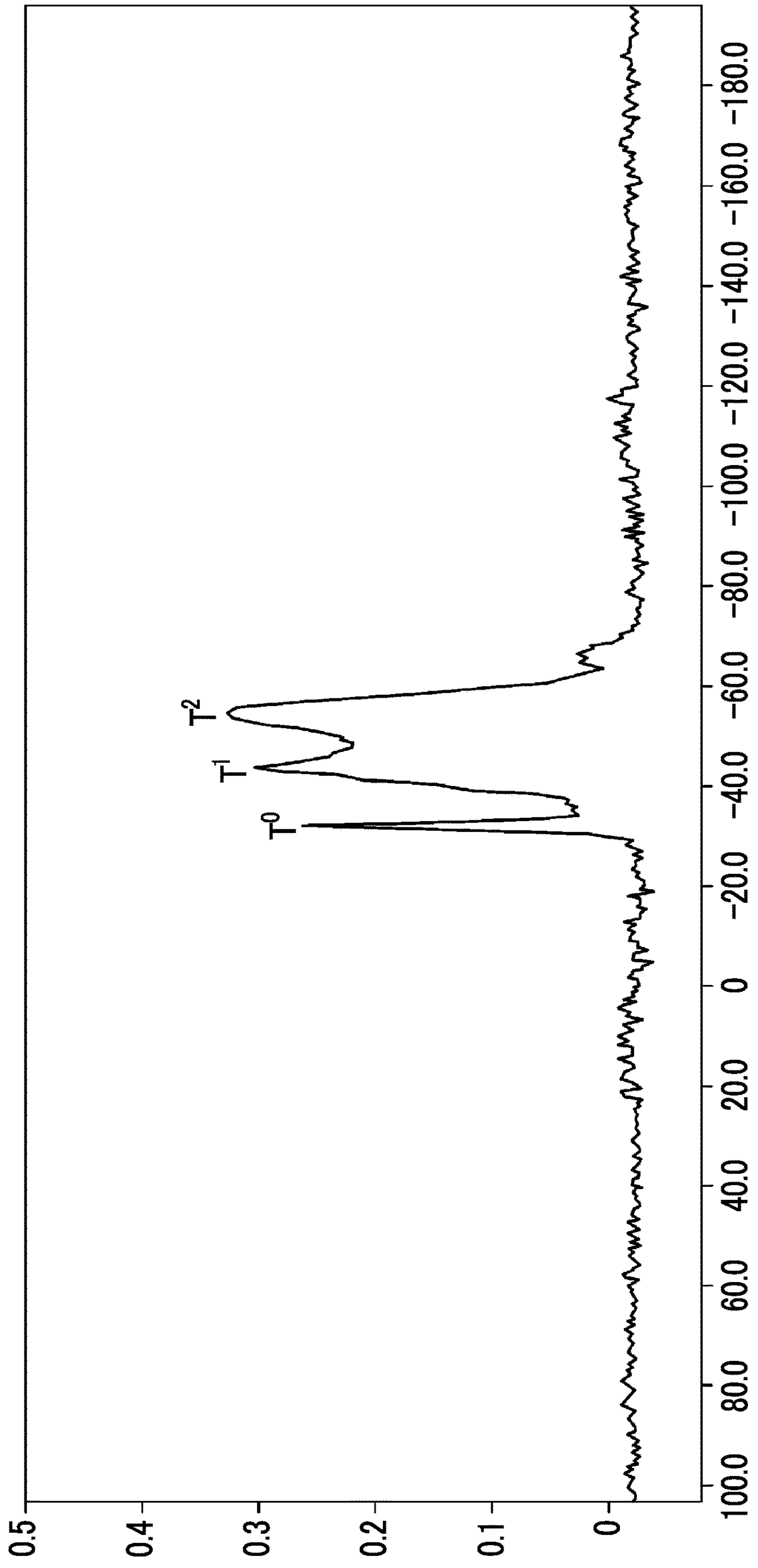
FIG. 2 is a view showing an NMR spectrum of the surface-treated zinc oxide particles of Example 1.
Figure 3:
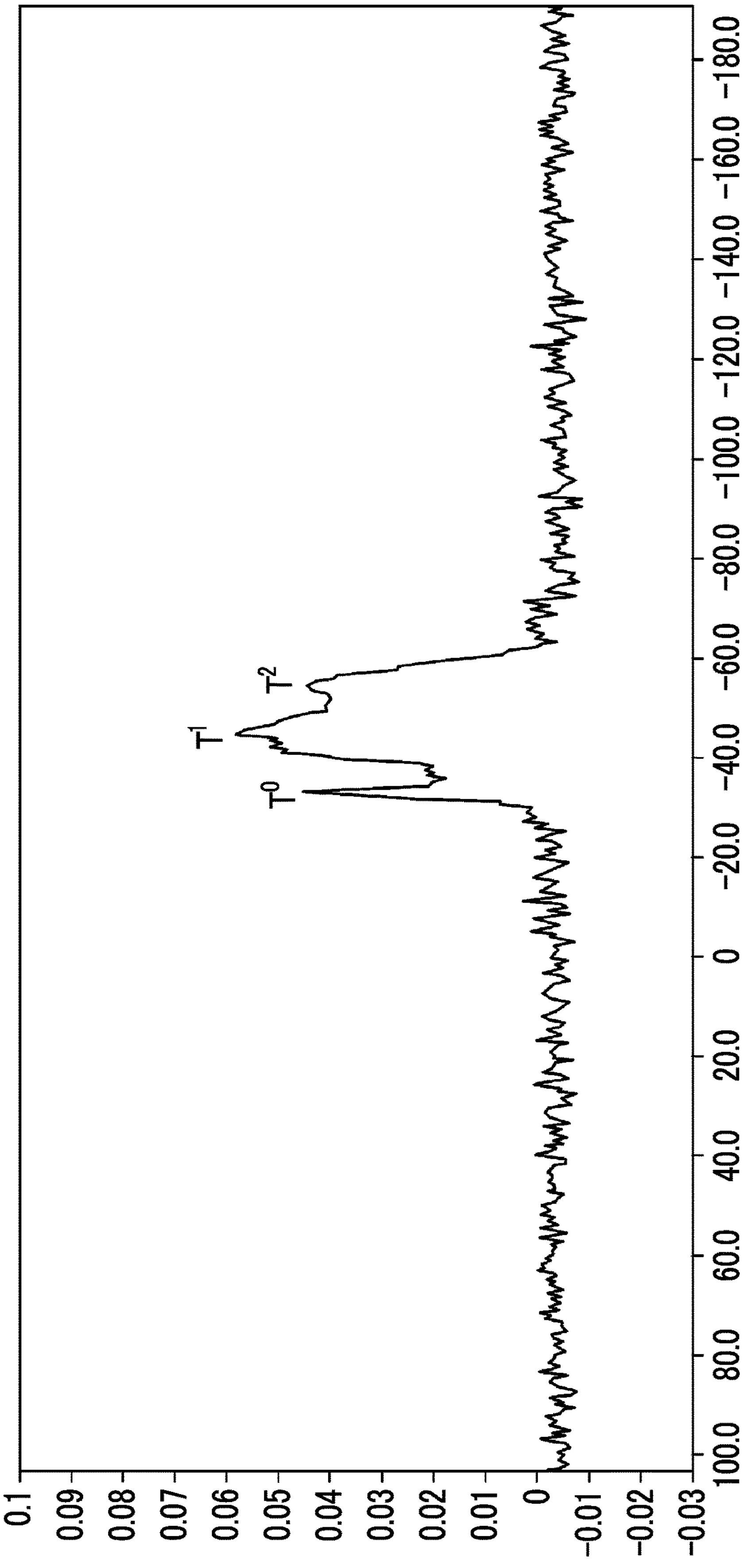
FIG. 3 is a view showing an NMR spectrum of the surface-treated zinc oxide particles of Comparative Example 1.

The spectra of the surface-treated zinc oxide particles obtained in Example 1 to Example 7, Comparative Example 1, and Comparative Example 2 were measured by the solid-state $^{29}$Si CP/MAS-nuclear magnetic resonance (NMR) spectroscopy (measurement conditions: CPMAS method, observation frequency: 79.42 MHz, observation width: 23.83 KHz, contact time: 5 ms, specimen rotation speed: 5 KHz, measurement temperature: 27° C., pulse delay: 5 s, and number of integrations: 16000). The measurement result of Example 1 is shown in FIG. 2. The measurement result of Comparative Example 1 is shown in FIG. 3.

When the integral value of the spectrum within a measurement range of −30 ppm to −60 ppm was defined as 100, the integral proportion of the spectrum within a measurement range of −30 ppm to −40 ppm was defined as A, the integral proportion of the spectrum within a measurement range of −40 ppm to −50 ppm was defined as B, and the integral proportion of the spectrum within a measurement range of −50 ppm to −60 ppm was defined as C. Surface-treated zinc oxide particles having C/B of 0.5 or more and 5.0 or less were evaluated as “0 (favorable)”, and surface-treated zinc oxide particles having C/B of less than 0.5 were evaluated as “X (unavailable)”. The results are shown in Table 1.

TABLE 1

| | Presence or absence of FT-IR peak | Weight loss on drying [% by mass] | D98 [μm] | BET specific surface area [m²/g] | Converted diameter [nm] | D98/converted diameter | Touch-and-feel (rough) | SPF value | C/B |
|---|---|---|---|---|---|---|---|---|---|
| Example 1 | Absent | 0.10 | 30 | 25 | 43 | 0.70 | ○ | 55 | ○ |
| Example 2 | Absent | 0.10 | 45 | 25 | 43 | 1.05 | ○ | 50 | ○ |
| Example 3 | Absent | 0.20 | 35 | 40 | 27 | 1.31 | ○ | 75 | ○ |
| Example 4 | Absent | 0.30 | 50 | 40 | 27 | 1.87 | ○ | 70 | ○ |
| Example 5 | Absent | 0.20 | 40 | 55 | 19 | 2.06 | ○ | 75 | ○ |
| Example 6 | Absent | 0.10 | 20 | 16 | 67 | 0.30 | ○ | 52 | ○ |
| Example 7 | Absent | 0.10 | 20 | 5 | 214 | 0.09 | ○ | 40 | ○ |
| Comparative Example 1 | Present | 0.60 | 60 | 25 | 43 | 1.40 | ○ | 27 | X |
| Comparative Example 2 | Absent | 0.10 | 150 | 40 | 27 | 5.61 | X | 60 | ○ |

(Evaluation of Touch-and-Feel)

The touch-and-feels of the surface-treated zinc oxide particles obtained in Example 1 to Example 7, Comparative Example 1, and Comparative Example 2 were evaluated as described below. The presence or absence of a rough feeling when the surface-treated zinc oxide particles were held with the thumb and index finger and rubbed together was evaluated. Surface-treated zinc oxide particles from which a rough feeling was not felt were evaluated as “0 (available)”, and surface-treated zinc oxide particles from which a rough feeling was felt were evaluated as “X (unavailable)”. The results are shown in Table 1.

(Measurement of SPF Value)

The dispersion liquids obtained in Example 1 to Example 7, Comparative Example 1, and Comparative Example 2 were each applied onto a quartz glass plate so that the thickness of the dispersion liquid became 12 μm and naturally dried for 15 minutes, thereby forming a coated film.

The obtained coated films were evaluated using an SPF analyzer UV-20005 (manufactured by Labsphere), and SPF values were obtained. The results are shown in Table 1.

From the surface-treated zinc oxide particles of Example 1 to Example 7, peaks were not detected at all of 1170 $cm^{-1}$, 1100 $cm^{-1}$, 1080 $cm^{-1}$, and 950 $cm^{-1}$. From the surface-treated zinc oxide particles of Comparative Example 1, peaks were detected at 1170 $cm^{-1}$, 1100 $cm^{-1}$, 1080 $cm^{-1}$, and 950 $cm^{-1}$. That is, it was confirmed that the SPF values were higher in the surface-treated zinc oxide particles of Example 1 to Example 7 than in the surface-treated zinc oxide particles of Comparative Example 1 from which the peaks were detected.

In addition, it was confirmed that the SPF values were higher in the surface-treated zinc oxide particles of Example 1 to Example 7 in which the weight loss on drying at 105° C. for 3 hours was 0.5% by mass or less in the surface-treated zinc oxide particles of Comparative Example 1 in which the weight loss on drying exceeded 0.5% by mass.

In addition, it was confirmed that rough feelings were more suppressed in the surface-treated metal oxide particles of Example 1 to Example 7 in which the D98/converted diameter was 0.01 or more and 5.0 or less in the surface-treated metal oxide particles of Comparative Example 2 in which the D98/converted diameter was 5.61.

In addition, in Examples 1 to 7 and Comparative Example 2, C/B was 0.5 or more and 5.0 or less. In Comparative Example 1, C/B was less than 0.5. It was confirmed that the SPF values were higher in the surface-treated metal oxide particles of Example 1 to Example 7 in which the value (C/B) was 0.5 or more and 5.0 or less in Comparative Example 1 in which the divided value (C/B) was less than 0.5.

INDUSTRIAL APPLICABILITY

The surface-treated metal oxide particles of the present invention stably exhibit a high ultraviolet shielding property and suppress a rough feeling. Therefore, the surface-treated metal oxide particles of the present invention easily guarantee the design quality in the case of being applied to dispersion liquids, compositions, paints, and cosmetics and have great industrial values.

The invention claimed is:

1. Surface-treated metal oxide particles surface-treated with a silane coupling agent having an alkoxy group, wherein the metal oxide particles have an ultraviolet shielding property, a weight loss of the surface-treated metal oxide particles on drying at 105° C. for 3 hours is 0.5% by mass or less, wherein the weight loss is determined by measuring a weight difference of the surface-treated metal oxide particles before and after drying, a peak derived from the alkoxy group of the silane coupling agent having an alkoxy group is not detected in 900 $cm^{-1}$ to 1300 $cm^{-1}$ in a reflection spectrum of the surface-treated metal oxide particles, which is measured by a Fourier transform infrared spectrophotometer, and a ratio of a dry particle size D98 (μm) of the surface-treated metal oxide particles to a BET-converted particle diameter (nm) of the surface-treated metal oxide particles is 0.01 or more and 5.0 or less.

2. The surface-treated metal oxide particles according to claim 1, wherein the metal oxide particles are at least one selected from the group consisting of zinc oxide particles, titanium oxide particles, and cerium oxide particles.

3. The surface-treated metal oxide particles according to claim 1, wherein the silane coupling agent having an alkoxy group is a compound represented by a following formula (3), $$R^1Si(OR^2)_3 \quad (3)$$

($R^1$ represents a phenyl group, or a fluoroalkyl group or an alkyl group having 1 to 18 carbon atoms, and $R^2$ represents an alkyl group having 1 to 4 carbon atoms).

4. The surface-treated metal oxide particles according to claim 1, wherein the silane coupling agent having an alkoxy group is octyltriethoxysilane.

5. The surface-treated metal oxide particles according to claim 1, wherein whether or not the surface-treated metal oxide particles have the ultraviolet shielding property is determined by the following evaluation:

a film which has a thickness after drying of 12 μm is prepared by applying a dispersion liquid containing 10 parts by mass of the metal oxide particles;

a transmission spectrum of the film is measured to obtain an average transmittance A of the film within a range of 250 nm to 400 nm and a transmittance B of the film at 450 nm; and the surface-treated metal oxide particles are determined to have the ultraviolet shielding property in a case where the transmittance A is lower than the transmittance B.

6. The surface-treated metal oxide particles according to claim 1, wherein, when a spectrum of the surface-treated metal oxide particles is measured by a solid-state $^{29}Si$ CP/MAS-nuclear magnetic resonance (NMR) spectroscopy and an integral value of the spectrum within a measurement range of −30 ppm to −60 ppm is defined as 100, a ratio of an integral proportion of the spectrum within a measurement range of −50 ppm to −60 ppm to an integral proportion of the spectrum within a measurement range of −40 ppm to −50 ppm is 0.5 or more and 5.0 or less.

7. A dispersion liquid comprising:

the surface-treated metal oxide particles according to claim 1; and a dispersion medium.

8. A cosmetic comprising:

at least one kind of the surface-treated metal oxide particles according to claim 1.

9. The cosmetic according to claim 8, further comprising:

a dispersion medium.

10. A method for producing the surface-treated metal oxide particles surface-treated with a silane coupling agent having an alkoxy group according to claim 1, wherein the surface-treated metal oxide particles have an ultraviolet shielding property, the method comprising:

a step of preparing surface-treated metal oxide particles surface-treated with a silane coupling agent having an alkoxy group;

a step of measuring the surface-treated metal oxide particles with a Fourier transform infrared spectrophotometer to obtain a reflection spectrum thereof in 900 $cm^{-1}$ to 1300 $cm^{-1}$; and a step of determining whether or not a peak derived from the alkoxy group is detected in the reflection spectrum.

11. The method for producing surface-treated metal oxide particles according to claim 10, wherein when the peak derived from the alkoxy group is confirmed in the step of determining whether or not a peak derived from the alkoxy group is detected, the method further comprising:

a step of heating the surface-treated metal oxide particles until the peak is not detected any longer.

12. The method for producing surface-treated metal oxide particles according to claim 10, wherein the peak derived from the alkoxy group is located at 1170 $cm^{-1}$, 1100 $cm^{-1}$, 1080 $cm^{-1}$, and 950 $cm^{-1}$.

13. The method for producing surface-treated metal oxide particles according to claim 10, wherein the step of preparing the surface-treated metal oxide particles has a sub-step of preparing metal oxide particles and the silane coupling agent;

a sub-step of mixing the metal oxide particles and the silane coupling agent with each other to obtain a mixture;

a sub-step of heating the mixture; and a sub-step of treating the heated mixture by cracking until the particles are obtained, which satisfy 0.01 or more and 5.0 or less of D98 (μm)/BET converted diameter (nm).

14. The method for producing surface-treated metal oxide particles according to claim 10, wherein the step of preparing the surface-treated metal oxide particles has a sub-step of preparing metal oxide particles, the silane coupling agent, and a solvent;

a sub-step of mixing the metal oxide particles, the silane coupling agent, and the solvent with one another to obtain a mixture;

a sub-step of drying the mixture to remove the solvent and obtain the surface-treated metal oxide particles; and a sub-step of cracking the metal oxide particles from which the solvent had been removed, until the particles are obtained, which satisfy 0.01 or more and 5.0 or less of D98 (μm)/BET converted diameter (nm).

15. The method for producing surface-treated metal oxide particles according to claim 10, further comprising:

a step of determining whether or not a weight loss of the particles, which are prepared in the step of preparing the surface-treated metal oxide particles, on drying at 105° C. for 3 hours is 0.5% by mass or less; and a step of determining whether or not the particles, which are prepared in the step of preparing the surface-treated metal oxide particles, satisfy 0.01 or more and 5.0 or less of a value (D98 (μm)/BET-converted particle diameter (nm)), which is obtained by dividing a dry particle size D98 (μm) thereof by a BET-converted particle diameter (nm) thereof.

16. The method for producing surface-treated metal oxide particles according to claim 10, further comprising:

a step of determining whether or not the surface-treated metal oxide particles have the ultraviolet shielding property, wherein this step has the following sub-steps:

a sub-step of obtaining a film which is prepared by applying a dispersion liquid containing 10 parts by mass of the metal oxide particles so that a thickness thereof after drying becomes 12 μm;

a sub-step of measuring a transmission spectrum of the obtained film to obtain an average transmittance A of the film within a range of 250 nm to 400 nm and a transmittance B of the film at 450 nm; and a sub-step of determining that the surface-treated metal oxide particles have the ultraviolet shielding property, when the transmittance A is lower than the transmittance B.

17. The method for producing surface-treated metal oxide particles according to claim 10, wherein the surface-treated metal oxide particles produced are particles wherein a weight loss of the surface-treated metal oxide particles on drying at 105° C. for 3 hours is 0.5% by mass or less, a peak derived from the alkoxy group is not detected in a reflection spectrum of the surface-treated metal oxide particles in 900 $cm^{-1}$ to 1300 $cm^{-1}$, which is measured by a Fourier transform infrared spectrophotometer, and a value (D98 (μm)/BET-converted particle diameter (nm)) obtained by dividing a dry particle size D98 (μm) thereof by a BET-converted particle diameter (nm) thereof is 0.01 or more and 5.0 or less.

18. The method for producing surface-treated metal oxide particles according to claim 10, further comprising:

a step of measuring a spectrum of the particles which are prepared in the step of preparing the surface-treated metal oxide particles by a solid-state $^{29}$Si CP/MAS-nuclear magnetic resonance (NMR) spectroscopy, and determining whether or not a value obtained by dividing an integral proportion of the spectrum within a measurement range of −50 ppm to −60 ppm by an integral proportion of the spectrum within a measurement range of −40 ppm to −50 ppm is 0.5 or more and 5.0 or less, when an integral value of the spectrum within a measurement range of −30 ppm to −60 ppm is defined as 100.

* * * * *